(12) United States Patent
Yamamoto et al.

(10) Patent No.: US 6,933,135 B1
(45) Date of Patent: Aug. 23, 2005

(54) ANTIBODIES SPECIFIC FOR INTRACELLULAR DOMAIN OF PROTEIN TYROSINE PHOSPHATASE

(75) Inventors: Hiroshi Yamamoto, Toyonaka (JP); Kazutake Tsujikawa, Kawanishi (JP); Yukiko Uchino, Osaka (JP)

(73) Assignee: Fuso Pharmaceutical Industries Ltd., Osaka (JP)

( * ) Notice: Subject to any disclaimer, the term of this patent is extended or adjusted under 35 U.S.C. 154(b) by 0 days.

(21) Appl. No.: 09/743,492

(22) PCT Filed: Jul. 6, 1999

(86) PCT No.: PCT/JP99/03656

§ 371 (c)(1),
(2), (4) Date: Apr. 30, 2001

(87) PCT Pub. No.: WO00/02922

PCT Pub. Date: Jan. 20, 2000

(30) Foreign Application Priority Data

Jul. 10, 1998 (JP) .................................. PCT/JP98/03120

(51) Int. Cl.[7] .......................... C12P 21/04; C12N 5/16; C07K 16/28
(52) U.S. Cl. ..................... 435/69.6; 435/70.1; 435/326; 530/388.22
(58) Field of Search .................. 530/387.1, 388.22; 435/326, 69.6, 70.1

(56) References Cited

U.S. PATENT DOCUMENTS

| | | | |
|---|---|---|---|
| 4,752,583 A | * | 6/1988 | Jensen et al. |
| 5,538,886 A | | 7/1996 | Schlessinger et al. |
| 5,646,333 A | * | 7/1997 | Dobres et al. |
| 5,736,149 A | * | 4/1998 | Avjioglu et al. |
| 5,837,505 A | * | 11/1998 | Della-Cioppa et al. |
| 5,888,794 A | * | 3/1999 | Schlessinger et al. |
| 5,916,561 A | * | 6/1999 | Adolf et al. |

FOREIGN PATENT DOCUMENTS

EP  1 097 944 A1  4/2001

OTHER PUBLICATIONS

Debant A, Serra–Pages C, Seipel K, O'Brien S, Tang M, Park SH, Streuli M. The multidomain protein Trio binds the LAR transmembrane tyrosine phosphatase, contains a protein kinase domain, and has separate rac–specific guanine nucleotide exchange factor domains. Proc. Natl Acad Sci USA 93(11):5466–5471, 1996.*
Bost KL, Pascual DW. Antibodies against a peptide sequence within the HIV envelope protein crossreacts with human interleukin–2. Immunol Invest. Aug.–Oct. 1988;17(6–7):577–86.*
Harlow E, Lane D. 1988. Antibodies a laboratory manual. Cold Spring Harbor, New York: Cold Spring Harbor Laboratory Press.*
Hersh D, Monack DM, Smith MR, Chori N, Falkow S, Zychlinsky A Salmonella invasin SipB induces macrophage apoptosis by binding to caspase–1. Proc Natl Acad Sci U S A. Mar. 2, 1999;96(5):2396–401*
Bendayan M. Possibilities of false immunocytochemical results generated by the use of monoclonal antibodies: the example o the anti–proinsulin antibody. J Histochem Cytochem. 43(9):881–6, 1995.*
Besco JA et al. Genomic organization and alternative splicing of the human and mouse RPTPrho genes. BMC Genomics. 2(1):1, 2001.*
Furukawa et al., "Specific Interaction of the CD45 Protein–Tyrosine Phosphatase with Tyrosine–Phosphorylated CD3 ζ Chain", *Proc. Natl. Acad. Sci. USA*, 91:10928–10932(1994).
Goldstein et al., "Regulation of Insulin Receptor Signaling by Protein–Tyrosine Dephosphorylation", *Receptor*, 3:1–15(1993).
Streuli et al., "A New Member of the Immunoglobulin Superfamily That Has a Cytoplasmic Region Homologous To The Leukocyte Common Antigen", *J. Exp. Med.*, 168:1523–1530(1988).
Streuli et al., "Expression of the Receptor–Linked Protein Tyrosine Phosphatase LAR: Proteolytic Cleavage and Ahedding of the CAM–Like Extracellular Region", *EMBO J.*, 11:897–907(1992).
Zhang et al., "Molecular Cloning and Expression of a Unique Receptor–Like Protein–Tyrosine–Phosphatase in the Leukocyte–Common–Antigen–Related Phosphatase Family", *Biochem. J.*, 302:39–47(1994).
Faure, et al., "Diagnostic Features of Primary Malignant Lymphomas of the Thyroid with Monoclonal Antibodies," *Cancer* (Phila.), 61(9):1852–1861 (1988).
Fernando, et al., "Monoclonal Antibodies to the Human γ2 Subunit of the GABA$_A$/Benzodiazepine Receptors," *J. Neurochem.*, 64(3):1305–1311 (1995).
Streuli et al., "Distinct Functional Roles of the Two Intracellular Phosphatase Like Domains of the Receptor–Linked Protein Tyrosine Phosphatases LCA and LAR," *EMBO J.*, 9(8):2399–2407 (1990).

(Continued)

*Primary Examiner*—Christina Chan
*Assistant Examiner*—Maher Haddad
(74) *Attorney, Agent, or Firm*—Marshall, Gerstein & Borun LLP

(57) ABSTRACT

Antibodies to intracellular domains of two or more kinds of protein tyrosine phosphatases, methods for generation thereof and cells producing these antibodies are disclosed. The antibody of the present invention may have specificity to intracellular domains of phosphatase subunits of both of LAR and CD45, and may be useful for analysis and quantitative determination of PTPs, identification and detection of novel PTPs, and for obtaining novel phosphatases by cloning and the like, as well as for developing useful diagnostic methods of insulin resistance and NIDDM, for prophylaxis and diagnosis of various disease states of syndrome X that is based on insulin resistance, and for prophylaxis and diagnosis of onsets of arteriosclerosis and cardiac diseases.

15 Claims, 10 Drawing Sheets

OTHER PUBLICATIONS

Takeuchi et al., "Characterization of AE–6 Monoclonal Antibody Recognizing VHCSAGV Sequence in CD45 PTPase Domain," *Tissue Antigens*, 42(4):441 (1993). Abstract.

U.S. Appl. No. 09/718,272, filed May 3, 2001, Yamamoto, et al.

Osamu Kanemitsu, "Koutai Kougaku Nyuumon," *K.K. Chijin Shokan*, 145–166 (1994).

Ahmad, et al., "Increased Abundance of the Receptor–type Protein–Tyrosine Phosphatase LAR Accounts for the Elevated Insulin Receptor Dephosphorylating Activity in Adipose Tissue of Obese Human Subjects," *J. Clin. Invest.*, 95:2806–12 (1995).

Ahmad, et al., "Functional Association between the Insulin Receptor and the Transmembrane Protein–tyrosine Phosphatase LAR in Intact Cells," *J. Biol. Chem.*, 272(1):448–57 (1997).

Yakura, "CD45 Isoforms and Functional Diversity of T and B Cells," *Medical Immunology*, 27(4):333–339 (1994). (English translation of Table 1 on p. 334).

Itoh et al., "Purification and Characterization of the Catalytic Domains of the Human Receptor–linked Protein Tyrosine Phosphatases HPTPβ, Leukocyte Common Antigen (LCA), and Leukocyte Common Antigen–related Molecule (LAR)," J. Bio. Chem. 267:17, pp. 12356–12363, 1992.

Yu et al., "The N–terminal and C–terminal Domains of a Receptor Tyrosine Phosphatase are Associated by Non–covalent Linkage," Oncogene v. 7, 1051–1057, 1992.

Zhang et al., "LAR Tyrosine Phosphatase Receptor: Alternative Splicing is Preferential to the Nervous System, Coordinated with Cell Growth and Generates Novel Isoforms Containing Extensive CAG Repeats," J. Cell. Bio. 128:3, 415–431, 1995.

* cited by examiner

```
LAR  : SNLEVNKPKNRYANVIAYDHSRVILTSIDGVPGSDYINANYIDGYRKQNAYIATQGPLPE   60
CD45 : ARKPFNQNKNRYVDILPYDYNRVELSEINGDAGSNYINASYIDGFKEPRKYIAAQGPRDE   60
        *• ****•••••**••**•*•••*•* •**•****•****•****•••• ***•*** *
              (1)                    (2)
LAR  : TMGDFWRMVWEQRTATVVMMTRLEEKSRVKCDQYWPAR--GTETCGLIQVTLLDTVELAT  118
CD45 : TVDDFWRMIWEQKATVIVMVTRCEEGNRNKCAEYWPSMEEGTRAFGDVVVKINQHKRCPD  120
        *••*****•***•••••**•**•**•••*•***•***** ** • * •***• •••  •
                                  (3)
LAR  : YTVRTFA-LHKSGSSEKRELRQFQFMAWPDHGVPEYPTPILAFLRRVKACNPLDAGPMVV  177
CD45 : YIIQKLNIVNKKEKATGREVTHIQFTSWPDHGVPEDPHLLLKLRRRVNAFSNFFSGPIVV  180
        *•••••••••*•••••••**• ••**•**********  •*  •  ***•*•• ••**•**
        (4)
LAR  : HCSAGVGRTGCFIVIDAMLERMKHEKTVDIYGHVTCMRSQRNYMVQTEDQYVFIHEALLE  237
CD45 : HCSAGVGRTGTYIGIDAMLEGLEAENKVDVYGYVVKLRRQRCLMVQVEAQYILIHQALVE  240
        ********** •* *******  •* •***•***•••• •• •*• *****•*• •*•**•*

LAR  : AATCGHTEVPARNLYAHIQKLGQVPPGESVTAMELEFKLLASSKAHTSRFISANLPCNKF  297
CD45 : YNQFGETEVNLSELHPYLHNMKKRDPPSEPSPLEAEFQRLPSYRSWRTQHIGNQEE-NKS  299
         • *•***  ••*•••••••  •  * •• •••* **• *•* ••  •• *••• **

LAR  : KNRLVNIMPYELTRVCL---------------QPIRGVEGSDYINASFLDGYRQQK    338
CD45 : KNRNSNVIPYDYNRVPLKHELEMSKESEHDSDESSDDDSDSEEPSKYINASFIMSYWKPE 359
        *** *•••**• •** *              •  • * *•*******• •*•••••
                (1)                       (2)
LAR  : AYIATQGPLAESTEDFWRMLWEHNSTIIVMLTKLREMGREKCHQYWPAERSARYQYFVVD  398
CD45 : VMIAAQGPLKETIGDFWQMIFQRKVKVIVMLTELKHGDQEICAQYWGEGKQT-YGDIEVD  418
        • **•*******••• *****•*•••**•**•*******•**•*****• • • •  **
                                          (3)
LAR  : PMAEYNMPQYILREFKVTDARDGQSRTIRQFQFTDWPEGGVPKTGEGFIDFIGQV-----  453
CD45 : LKDTDKSSTYTLRVFELRHSKRKDSRTVYQYQYTNWSVEQLPAEPKELISMIQVVKQKLP  478
        ••••• •** ••**•*••• ••• •***•***•**••***•••*•• ••*••*•***•-
                                  (4)
LAR  : ---HKTKEQFGQDGPITVHCSAGVGRTGVFITLSIVLERMRYEGVVDMFQTVKTLRTQRP  510
CD45 : QKNSSEGNKHHKSTPLLIHCRDGSQQTGIFCALLNLLESAETEEVVDIFQVVKALRKARP  538
         •• •• •••**•**•*•*•**•**••**••*•*•**•*•******•***•*****•*•**

LAR  : AMVQTEDQYQLCYRAALEYLGSFDHYAT--------------------------       538
CD45 : GMVSTFEQYQFLYDVIASTYPAQNGQVKKNNHQEDKIEFDNEVDKVKQDANCVNPLGAPE  598
        •** * •***• *

LAR  : ---------------------
CD45 : KLPEAKEQAEGSEPTSGTEGPEHSVNGPASPALNQGS                         639
```

Fig. 9

ANTIBODIES SPECIFIC FOR INTRACELLULAR DOMAIN OF PROTEIN TYROSINE PHOSPHATASE

FIELD OF THE INVENTION

The present invention relates to antibodies that specifically bind to intracellular domains of two or more kinds of protein tyrosine phosphatases (hereinafter referred to as PTPs) and to methods for generating the same. More particularly, the present invention relates to antibodies having specificity to intracellular domains of PTPs (e.g., LAR (leukocyte antigen related molecule) and CD45), which are useful for analysis and quantitative determination of PTPs, for identification, detection, and isolation and purification of novel PTPs, and for development of medical drugs applicable to treatments such as therapy, prevention and alleviation as well as diagnosis of the disease states associated with insulin resistance.

BACK GROUND OF THE INVENTION

Mechanisms involving in the onset of arteriosclerosis have been gradually elucidated in these days, and risk factors thereof have been identified. Especially, hypercholesterolemia, hypertension, diabetes, and smoking are recognized to be manifest four risk factors, thus the therapeutic treatments have been extensively carried out. Clinically common pathology of these disease states is insulin resistance. The meaning of insulin resistance is nearly equivalent to the reduction of sensitivity to insulin in cells, and may be that the actions of insulin upon the uptake of sugar into the cells are deteriorated. The insulin resistance may be caused due to the abnormalities in secretion of insulin itself, abnormalities of insulin receptors on target cells, abnormalities of an intracellular signaling system, and reduced supply of sugar to the tissue based on peripheral circulatory disorder that is caused hemodynamically. Reaven, in 1988, reported that many pathological states are developed due to the insulin resistance, and designates a pathological state as "syndrome X" that may concurrently represent insulin resistance, glucose tolerance abnormalities, hyperinsulinemia, hypertriglyceridemia, hypo-HDL cholesterolemia and hypertension, and further suggests that the pathological state syndrome X closely participates in the onset of arteriosclerosis (Reaven, G. M. et al., *Diabetes*, 37, 1595–1607, 1988).

In addition, sugar supply to the cells is known to be generally decreased through insulin resistance, accompanied by enhancement of insulin secretion from pancreas, thus leading to hyperinsulinemia. Therefore, several problems in connection with insulin resistance have been raised in clinical fields. For example, insulin resistance and hyperinsulinemia are reported to promote diabetic nephritis (Niskanen, L. et al., *Diabetes*, 41, 736–741, 1993), and to elevate frequency of diabetic retinopathy (Yip, J. et al., *Lancet*, 341, 369–370, 1993). Moreover, insulin resistance has been reported to enhance plasminogen activator inhibitor 1 (PAI-1), to deteriorate the functions of a blood fibrinolytic system (Potter van Loon B J et al., *Metab. Clin. Exp.*, 42, 945–954, 1993), and to trigger arterial atherosclerosis (Sato, Y. et al., *Diabetes*, 38, 91–96, 1989).

Prevalence rate of diabetes accounts for 5% of the total population, and approximately six millions of Japanese citizens are suffering from diabetes. Diabetes comprises insulin dependent diabetic mellitus (IDDM) and non-insulin dependent diabetic mellitus (NIDDM). Reportedly, IDDM accounts for about 7% of the total diabetes cases, whilst NIDDM does about 90%. In particular, a significant causative factor of the onset of NIDDM that corresponds to a majority of diabetes has been conceived as the insulin resistance.

To date, tyrosine phosphorylation of intracellular proteins has been elucidated to play important roles in signal transduction of insulin. Insulin receptor is a hetero-tetramer of two glycoprotein subunits, namely an α-subunit having a molecular weight of 135 kDa and a β-subunit having a molecular weight of 95 kDa, which are bound through disulfide bonds resulting in a hetero tetramer having an $\alpha 2\beta 2$ structure. The α-subunit has an insulin binding activity, while the β-subunit has a protein tyrosine kinase (PTK) domain that is activated by autophosphorylation. Accordingly, when insulin is bound to the α-chain of an insulin receptor, certain tyrosine residues existing in the β-chain of the insulin receptor are autophosphorylated by tyrosine kinase activity of the receptor. The activity of insulin receptor tyrosine kinase is further promoted through the tyrosine autophosphorylation. It is reported that thus activated insulin receptor tyrosine kinase phosphorylates tyrosine residues of IRS (insulin receptor substrate), the intracellular substrates thereof, and signal transduction is proceeded through recognition and binding of the tyrosine-phosphorylated insulin receptors by Ash/Grb2 or PI-3 kinase, finally resulting in manifestation of biological activities of insulin, such as glucose uptake, sugar metabolism and cell proliferation (see, FIG. 9, Goldstein, B. J. et al., *Receptor*, 3, 1–15, 1993, and Kanai, F. et al., *Biochemical and Biophysical Research Communications*, 195 (2), 762–768, 1993). In this signal transduction pathway, however, an enzyme that inactivates the activated insulin receptors, i.e., PTP, which is a protein tyrosine phosphatase, has not been progressively studied.

Moreover, fundamental mechanisms for lymphocyte activation, proliferation, differentiation, cell death and the like, which are also ingeniously controlled by tyrosine phosphorylation have not been likewise elucidated. Studies on signal transduction of lymphocyte in light of PTK have been mainstream of the studies so far, however, analyses from PTPs have also been performed, and importance of studies from both aspects have been manifested.

The serious studies of PTPs were initiated after completion of cloning of PTP1B gene and elucidation of the nucleotide sequence thereof by Fischer et al. in 1988, which is cytoplasm type PTP derived from human placenta (Tonks, N. K. et al., *J. Biol. Chem.*, 263, 6722–6730, 1988, Charbonneau, H. et al., *Proc. Natl. Acad. Sci. USA*, 85, 7182–7186, 1988). Consequently, homology to PTP1B could be observed not with the known serine/threonine phosphatases but with two cytoplasmic regions of CD45, a transmembranous molecule involved in a hemopoietic system. Moreover, CD45 was also revealed to have PTP activities (Tonks, N. K. et al., *Biochemistry*, 27, 8695–8701, 1988; and Charbonneau, H. et al., *Proc. Natl. Acad. Sci. USA*, 85, 7182–7186, 1988).

It is presumed that there are as many as 500 PTP genes in human, and to date, not less than 80 kinds of PTPs were cloned based on their homologies of cDNA sequences, while new PTPs have been still reported subsequently (Streuli, M. et al., *J. Exp. Med.*, 168, 1523–1530, 1988; Krueger, N. X. et al., *EMBO J.*, 9, 3241–3252, 1990; and Trowbridge, I. S. et al., *Biochim. Biophys. Acta*, 1095, 46–56, 1991). The PTPs that form a superfamily are broadly classified to three families. Namely, there are three groups, PTP, DS-PTP (dual-specificity-PTP) and LMW-PTP (low molecular weight-PTP). Homologies between primary structure of each of the family members are not that high, and in particular, no homology was suggested between PTP and LMW-PTP except for the homology of both enzymatic active centers, however, based on the studies on crystallography, it was illustrated that the molecules belonging to these families exhibit surprisingly common characters in their tertiary structures (Fauman, E. B. et al., *Trends Biochem. Sci.*, 21, 413–417, 1996). Furthermore, PTPs can be classified generally to: (1) receptor type (or, membrane type) PTPs having transmembrane region (LCA, leukocyte common antigen, namely CD45, LAR and PTPs α, β, γ, δ, ε and ζ); and (2) cytoplasm type PTPs without transmembrane region (PTP1B, TC-PTP, PTP-MEG, PTPH1, STEP, PTP1C, FAP1, SHP1, SHP2, PEP, PTP-PEST and the like).

Many of receptor type PTPs have two PTP homologous domains inside the cell (domain 1 and domain 2, see, FIG. 1(a) and (b)). A sequence comprising cysteine (signature motif), Ile/Val-His-Cys-Xaa-Ala-Gly-Xaa-Xaa-Arg-Ser/Thr-Gly (SEQ ID NO: 2), has been conserved in the phosphatase domains between the PTPs reported heretofore. The researches on crystallography of PTP1B revealed that the region forms small pockets on the surface of a PTP molecule, and that the cysteine residue is located to the bottom of the pocket, participating directly in binding of the molecule to phosphate (Barford, D. et al., *Science*, 263, 1397–1404, 1994). In addition, it was also revealed that the depth of the pocket of PTP may determine the specificity of serine/threonine phosphatase because phosphate that is binding to serine or threonine cannot reach to the pocket of the enzymatic active center of PTP1B. Moreover, the importance of the above-mentioned signature motif in exhibiting the enzymatic activity has been elucidated from experiments of the mutants (Streuli, M. et al., *EMBO J.*, 9, 2399–2407, 1990). Taking into account of these observations, it has been conceived that the conserved cysteine in domain 1 may play an important role in exhibiting the enzymatic activity, and domain 2 may determine the substrate specificity of the enzyme.

Receptor type PTPs have two or one intracellular enzymatic region(s), and they can be classified to several groups in accordance with their properties of extracellular domains. There are: CD45 having one extracellular fibronectin type III domain and being highly modified with sugar chains; LAR, PTPδ and PTPσ having Ig-like domains and fibronectin type III domains; PTPμ and PTPκ having MAM (meprin, A5 antigen, PTPμ) at N-terminal ends; PTPγ and PTPζ having a carbonate dehydratase domain at N-terminal ends; and PTPα and PTPε having short extracellular domains, and any of these PTPs has two enzymatic regions. Meanwhile, any of PTPs having single enzymatic region for example, PTPβ, and CD148 (PTPη, DEP.1 and the like), is constituted from only fibronectin type III domains in its extracellular domain.

Cytoplasm type PTPs have one enzymatic region in principle, and have been classified to several groups based on their properties of non-enzymatic regions. Cytoplasm type PTPs may have SH2 region, PEST region, and band 4.1 region. DS-PTPs are enzymes that dephosphorylate serine or threonine as well as tyrosine residue, which may include Cdc25, MAP kinase phosphatase, VH-1 and the like. LMW-PTP is constituted from an enzymatic region alone, and its molecular weight is reported to be about 18 kDa.

Among the groups of PTPs, LAR derived from human is a prototype of receptor type protein tyrosine phosphatases, which was cloned from human placental genome library using a phosphatase domain of CD45, a receptor type protein tyrosine phosphatase, as a probe (Streuli M. et al., *J. Exp. Med.*, 168, 1553–1562, 1988). CD45 is specifically expressed on hemocytic cells, whilst LAR is expressed on the cells other than hemocytic cells, particularly in insulin sensitive organs such as liver and skeletal muscle (Goldstein B. J., *Receptor*, 3, 1–15, 1993). LAR is especially interesting among many types of receptor type PTPs due to its similarity of the extracellular domain to cell adhesion molecules. The entire structure of LAR is elucidated as having 150 kDa of extracellular E-subunit that consists of Ig-like domains and fibronectin type III domains, and 85 kDa of P-subunit (phosphatase subunit, set out in SEQ ID NO:1) comprising a transmembrane region and an intracellular domain having two phosphatase domains, which are covalently bound immediately outside of the cell membrane (see, FIG. 1, Streuli M. et al., *EMBO J.*, 11, 897–907, 1992). Additionally, LAR constitutes a subfamily together with PTPδ and PTPσ, and exists in peripheral portions of desmosomes (junctions with extracellular matrix through integrin) and in adherens junctions (intercellular adherent portions through cadherin), (Serra-Pages, C. et al., *EMBO J.*, 14, 2827–2838, 1995; Pulido, R. et al., *Proc. Natl. Acad. Sci. USA*, 92, 11686–11690, 1995; Kypta, R. M. et al., *J. Cell Biol.*, 134, 1519–1530, 1996; and Aicher, B. et al., *J. Cell Biol.*, 138, 681–696, 1997).

A large number of functional roles of LAR have been reported to date. For example, it was reported that: responses to neurotrophin are decreased in LAR deficient nerves (Yang, T. et al., 27th Annual Meeting of the Society for Neuroscience, New Orleans, La., USA, Oct. 25–30, 1997, *Society for Neuroscience Abstracts*, 23, 1–2, 1997), LAR homologues of *Drosophila* are predominantly expressed in nervous system, and the deficiency thereof results in delay of timely segregation of motor axon from nerve fascicle (Krueger, N. X. et al., *Cell*, 84, 611–622, 1996); poor development of mammary gland is observed upon disruption of the gene encoding a LAR enzyme domain (Schaapveld, R. Q. et al., *Dev. Biol.*, 188, 134–146, 1997); secretion of apolipoprotein B is decreased by suppression of the LAR activity (Phung, T. L. et al., *Biochemical and Biophysical Research Communications*, 237 (2), 367–371, 1997), and loss of expression of LAR diminishes the size of cholinergic nerve cells of prosencephalon basement, thus control by the cholinergic nerve cells at hippocampal dentate gyrus is deteriorated (Yeo, T. T. et al., *J. Neurosci. Res.*, 47 (3), 348–360, 1997). In such a manner, it has been gradually revealed that LAR is bearing several important roles in a living body. Furthermore at present, the most remarkable researches are directed to the relationships between LAR and insulin receptors (Hashimoto, N. et al., *J. Biol. Chem.*, 267 (20), 13811–13814, 1992).

In 1995, a literature was presented which should be noted, reporting that the LAR tyrosine phosphatase activity is abnormally increased in adipose tissue of an obese person, with such an increase being suggested as a cause of onset of insulin resistance and a risk factor of cardiovascular diseases (Ahmad, F. et al., *J. Clin. Invest.*, 95 (6) 2806–2812, 1995). Several reports followed thereafter illustrating that LAR is closely concerned with insulin receptors (Mooney, R. A. et al., *Biochemical and Biophysical Research Communications*, 235 (3), 709–712, 1997; Orr, S. R. et al., *Biochemical Society Transaction*, 25 (3), 452S, 1997; Ahmad, F. et al., *J. Clin. Investigation*, 100 (2), 449–458, 1997; Ahmad, F. et al., *J. Biol. Chem.*, 272 (1), 448–457, 1997; Norris, K. et al., *Febs Letters*, 415(3), 243–248, 1997; and Li, P. M. et al., *Cellular Signaling*, 8 (7), 467–473, 1996). Further, on the basis of such information, Ahmad, F.

et al. recently reported that PTP1B may be a therapeutic target of disease states involving in insulin resistance (Ahmad, F. et al., *Metabolism, Clinical and Experimental,* 46 (10), 1140–1145, 1997).

Next, CD45 among the PTPs, which is also called as leukocyte common antigen (LCA), is a cell surface antigen that is expressed on all hemocytes (leukocytes) other than mature erythrocytes and platelets, and precursor cells thereof CD45 is a receptor type PTP of which molecular weight ranging between 180 and 220 kDa, having two enzymatic regions intracellularly, and 8 to 9 kinds of isoforms exist which may result from alternative splicing of 3 to 4 exons proximate to N-terminal end of an extracellular region (Saga, Y. et al., *Proc. Natl. Acad. Sci. USA,* 84, 5364–5368, 1987; Thomas, M. L. et al., *Proc. Natl. Acad. Sci. USA,* 84, 5360–5363, 1987; and Trowbridge, I. S. et al., *Annu. Rev. Immunol.,* 12, 85–116, 1994). The amino acid sequences encoded by these exons that may be spliced are rich in serine, threonine and proline, and hardly forms the integrated three-dimensional structures based on α-helix, β-structures and the like, in addition, many O-glycosylated sites are included therein (Barclay, A. N. et al., *EMBO J.,* 6, 1259–1267, 1987). Therefore, CD45 may be characterized in that the structure of extracellular region can be greatly changed due to changes in the isoforms. Additionally, CD45 is highly expressed in lymphocytes, and intrinsic isomers may be expressed reversibly depending upon cell species, or states of activation of the cells (Thomas, M. L. et al., *Annu. Rev. Immunol.,* 7, 339–369, 1989; Charbonneau, H. et al., *Annu. Rev. Cell. Biol.,* 8, 402–493, 1992; and Trowbridge, I. S. et al., *Annu. Rev. Immunol.,* 12, 85–116, 1994). Furthermore, the sequence of a region, which is interposed between the alternative structures and a transmembrane region, comprises a lot of cysteine, and forms a stabilized structure through disulfide bonds (Thomas, M. L. et al., *Cell* 41, 83–93, 1985; Trowbridge, I. S. et al., *J. Biol. Chem.,* 266, 23517–23520, 1991; Trowbridge, I. S. et al., *Biochim. Biophys. Acta,* 1095, 46–56, 1991).

It is known that immunogen-specific responsiveness that was intrinsically possessed in the cells is remarkably lowered in variant T cell line with CD45 expression being lost, thus it is suggested that CD45 may be extremely important in activation of T cell via T cell receptors (TCR), and in functional expression thereof (Charbonneau, H. et al., *Annu. Rev. Immunol.,* 7, 339–369, 1989; Pingel, J. T. et al., *Cell,* 58, 1055–1065, 1989; Trowbridge, I. et al., *Annu. Rev. Immunol,* 12, 85–116, 1994; Koretzky, G. A. et al., *Nature,* 346, 66–68, 1990, Koretzky, G. A. et al., *Proc. Natl. Acad. Sci. USA,* 88, 2037–2041, 1991; and Weaver, C. T. et al., *Mol. Cell Biol.,* 11, 4415–4422, 1991). In addition, it is also suggested that CD45 may participate in activation of Lck (p56$^{lck}$) and Fyn (p56$^{fynT}$), which are tyrosine kinases (PTK) in Src family and are binding to intracellular domain of CD4 and CD8 that are co-receptors of CD45 (Trowbridge, I. S. et al., *Annu. Rev. Immunol.,* 12, 85–116, 1994; and Penninger, J. M. et al., *Immunol. Rev.,* 135, 183–214, 1993). CD45 dephosphorylates tyrosine residues at a negative regulatory site located in C-terminal end of Lck or Fyn, and consequently, it is believed that Lck or Fyn is autophosphorylated to yield its active form, thus resulting in signal transduction (Penninger, J. M. et al., *Immuno. Rev.,* 135, 183–214, 1993; Ledbetter, J. A. et al., *Curr. Opin. Immunol.,* 5, 334–340, 1993; Janeway, C. A. Jr., *Annu. Rev. Immunol.,* 10, 645–674, 1992; Cahir, McFarland, E. D. et al., *Proc. Natl. Acad. Sci. USA,* 90, 1402–1406, 1993; Hurley, T. R. et al., *Mol. Cell Biol.,* 13, 1651–1656, 1993; Sieh, M. et al., *EMBO J.,* 12, 315–321, 1993; Weiss, A. et al., *Cell,* 76, 263–274, 1994; and Chan, A. C. et al., *Annu. Rev. Immunol.,* 12, 555–592, 1994). From the experiments using CD45-deficient cell strain among insulin responsive myeloma cells, it was reported that autophosphorylation of insulin receptors, tyrosine phosphorylation of IRS-1, and activation of P13 kinase and activation of MAP kinase upon insulin stimulation were all enhanced to three fold in comparison with the strain expressing CD45 (Kulas, D. T. et. al., *J. Biol. Chem.,* 271, 755–760, 1996), therefore, CD45 is supposed to be a negative regulatory factor of insulin similarly to LAR. Moreover, responsiveness of CD45-deficient cells was demonstrated to be recovered upon expression of molecules having only an intracellular region of CD45 by the following experiments. Namely, it was elucidated that: an enzymatic activity of tyrosine phosphatase can be sufficiently observed even when only the intracellular region of CD45 was expressed in bacterial or baculoviral systems (Ostergaard, H. L. et al., *Proc. Natl. Acad. Sci. USA,* 86, 8959–8963, 1989; Streuli, M. et al., *Proc. Natl. Acad. Sci. USA,* 86, 8698–8702, 1989); and signaling madiated by antigen receptors can be recovered by simply transfecting an intracellular region of CD45 to a T cell clone that is negative in CD45 (Volarevic, S. et al., *Science,* 260, 541–544, 1993; Hovis, R. R. et al., *Science,* 260, 544–546, 1993; and Desai, D. M. et al., *Cell,* 73, 541–554, 1993).

Besides, also in cases of B cell, it was indicated that not only early stage of signal transduction, but also ultimate proliferation, or the processes leading to apoptosis may be regulated through CD45 expression, according to the experiments using plasma cell species without expressing CD45 (Justement, L, B. et al., *Science,* 252, 1839–1842, 1991), or the experiments using CD45-negative clone that was established from immature B cell strain (Ogimoto, M. et. al., *Int. Immunol.,* 6, 647–654, 1994). These results suggest that CD45 is a molecule that is bearing essential roles in antigen receptors-mediated signal transduction.

Accordingly, from the researches to date on PTPs such as LAR, CD45 and the like, it has been elucidated that PTPs bear extremely important roles in an intracellular signaling system, in conjunction with PTKs.

In 1992, Streuli et al., reported that binding between LAR E-subunit and P-subunit may be dissociated due to the noncovalency of their binding, and thus E-subunit is specifically shed from the cell membrane surface (Streuli, M. et al., *EMBO J.,* 11 (3), 897–907, 1992). However, because many researchers have focused the studies using polyclonal or monoclonal antibodies elicited against a LAR E-subunit that is an extracellular domain thereof, a P-subunit even solely having phosphatase activities has been ignored. For example, when an anti-LAR antibody is used intending measurement of activity of LAR phosphatase, total phosphatase activity cannot be measured unless an antibody to the P-subunit is employed. Further, there exist several isoforms in extracellular domains of LAR family resulting from different types of mRNA splicing (Krueger, N. X. et al., *Cell,* 84, 611–622, 1996; Mizuno, K. et al., *Mol. Cell Biol.,* 13, 5513–5523, 1993; and Ogata, M. et al., *J. Immunol.,* 153, 4478–4487, 1994), thus different specificity to each isoform may be achieved when an antibody to an extracellular domain is used. In view of such circumstances, the present inventors started to produce antibodies to intracellular domains of PTPs.

Meanwhile, anti-CD45 antibodies were conventionally discriminated to antibodies that exhibit specificity to any of the CD45 isoforms having different molecular weights such as T200 or B220, and the antibodies that exhibit specificity only to a particular and restricted isoform, where the latter antibodies have been designated as CD45R (restricted) antibody (McMichael, A. J., In *Leucocyte Typing III*. Oxford University Press, Oxford, 1987). However, as diversities of structure of the extracellular domain of CD45 have been clarified, needs for classification of the specificity of the CD45R antibodies have been raised. Streuli et al. classified known human CD45 antibodies by a method using cDNA transfectants, and proposed to refer to the antibody that recognizes the structure that depends on alternative exon 4, 5, or 6 as CD45RA, CD45RB or CD45RC respectively (Streuli, M. et al., *J. Immunol*, 141, 3910–3914, 1988). Using a similar method, Johnson et al. also reported classification of mouse CD45 antibodies (Johnson, P. et al.,*J. Exp. Med.,* 169, 1179–1184, 1989).

For further references, known antibodies to PTPs may include an antibody that was generated using 196 amino acid residues as an antigen spanning from the transmembrane (TM) region of CD45 to a part of phosphatase domain 1 (Transduction Laboratories), and an antibody to phosphatase domain 1 (260 amino acid residues) of PTPα (Transduction Laboratories). However, it is unclear how these antibodies are immunospecific to phosphatase domains of LAR, and the other PTPs.

SUMMARY OF THE INVENTION

One aspect of the present invention is to provide an antibody having specificity to intracellular domains of two or more kinds of PTPs, and in particular, an antibody having specificity to an intracellular domain of at least one or more receptor type PTP. Particularly, the antibody according to the present invention may be an antibody having specificity to intracellular domains of LAR and/or CD45, preferably both of the intracellular domains of LAR and CD45. The antibody may preferably have specificity to phosphatase domains of PTPs.

The above-described antibody may be preferably generated using a polypeptide corresponding to a P-subunit of LAR that is encoded by a nucleotide sequence set out in SEQ ID NO: 1 or any of fragments thereof as an antigen. Further, preferred antibody may be a monoclonal antibody because of its immunospecific property.

In addition, the antibody may be generated using a fusion protein comprising a protein tyrosine phosphatase domain and another protein or a polypeptide, as an immunogen. The protein tyrosine phosphatase domain that is a member of the fusion protein may preferably be a phosphatase domain of LAR, and as the another protein or the polypeptide, GST (glutathione-S-transferase) may be particularly suitable, besides, polyhistidine (preferably 6 histidine residues), calmodulin binding peptide (CBP), protein A and the like may be employed as the another protein or the polypeptide.

When polyhistidine is employed, absorption to nickel-chelating resin can be utilized for isolation and purification of the fusion protein expressed by a gene recombinant process, wherein addition of EDTA or imidazole substance as well as pH change may be adopted for dissociating the protein from the resin. When CBP is employed, the expressed fusion protein may be subjected to an affinity chromatography using calmodulin affinity resin, and then may be dissociated from the resin by adding EGTA. In addition, when protein A is employed, the expressed fusion protein may be subjected to an affinity chromatography using IgG sepharose (e.g., IgG Sepharose 6FF), and then may be dissociated from the resin by changing pH.

Moreover, another candidate for the protein or the polypeptide fragment to be employed in the fusion protein may include for example, Xpress, Thioredoxin, c-myc, V5, HA/c-myc and the like. For isolation and purification of the intended fusion protein with a LAR phosphatase domain, expression of the protein may be followed by subjecting to an antigen-antibody affinity column.

The aforementioned preferable immunogen of the present invention, namely a fusion protein of GST and a LAR phosphatase domain, may be suitably produced by: culturing *Escherichia coli* transformed or transfected with an expression vector comprising a coding region of GST gene and a coding region of a phosphatase domain of LAR gene at 20–30° C. for 16–24 hours, preferably at 23–25° C. for 18 hours; and then isolating the fusion protein from the culture fluid and/or bacterial cells. Thus obtained fusion protein may be further purified based on an affinity to a support carrying glutathione, e.g., glutathione sepharose beads, wherein the elution of the fusion protein from the glutathione sepharose beads may be performed by boiling in the presence of a detergent. The detergent may include sodium dodecyl sulfate, CHAPS (3-[(3-cholamide propyl) dimethylammonio]-1-puropane sulfonate), deoxycholic acid, digitonin, n-dodecylmaltoside (1-O-n-dodecyl-β-D-glucopyranosyl(1–4) α-D-glucopyranoside), Nonidet™ P40 (ethylphenolpoly(ethylene glycol ether)n), n-octylglucoside (1-O-n-octyl-β-D-glucopyranoside), sucrose monolaurate, Tesit™ (dodecylpoly(ethylene glycol ether)n), Triton™ X-100 (octylphenolpoly(ethylene glycol ether)n), Tween™ 20 (poly(oxyethylene) n-sorbitan-monolaurate), N-dodecyl-N,N-dimethyl-3-ammonio-1-propanesulfonate, and the like [any of 'n' represents an integer number which is more than or equal to 1]. When elution of the fusion protein is carried out, the resin may be boiled at 100° C. for 5–10 minutes in the presence of such detergents at a concentration that does not lead any problems to an animal to be administered, preferably in the presence 0.1% of sodium dodecylsulfate. Accordingly, a purified fusion protein, which is preferable as a contemplated immunogen, can be obtained.

When a monoclonal antibody is generated using such a fusion protein as an immunogen, a protein tyrosine phosphatase domain, preferably a LAR phosphatase domain may be employed for screening the antibody, however, it is more preferable to perform the screening using the fusion protein as an immunogen in terms of the specificity.

The monoclonal antibody of the present invention may include a monoclonal antibody that is produced from mouse/mouse hybridoma cells, and has specificity to intracellular domains of phosphatase subunits of LAR and CD45. For example, such an antibody of the present invention may include a monoclonal antibody having an apparent molecular weight of about 146 kDa on SDS-PAGE. The antibody can be applied as a tool for further elucidation of the mechanisms of an insulin signaling system, for developing useful diagnostic methods of insulin resistance and NIDDM, and for prophylaxis, therapeutics and diagnosis of several kinds of pathological states relating to syndrome X based on insulin resistance.

Further aspect of the present invention is to provide a hybridoma cell line producing the above-mentioned monoclosnal antibody. Such a hybridoma cell line may include mouse/mouse hybridoma cell line YU2, which was deposited on May 7, 1998, with National Institute of Bioscience and Human-Technology, Agency of Industrial Science and Technology, 1–1-320, Higashi, Tsukuba, Ibaraki, JAPAN, and assigned Accession No. FERM BP-6344.

The antibody of the present invention has specific immunoreactivity with PTP protein, and fragments and polypeptides that comprise at least a part (more than or equal to three amino acid residues, preferably, more than or equal to five amino acid residues) of an intracellular domain of PTP (the fragment and polypeptide are hereinafter collectively referred to as 'PTP derived molecules'), which was derived from natural sources, or wholly or partially synthesized (such as those chemically synthesized, or recombinantly synthesized).

Another aspect of the present invention is to provide a method for generating an antibody having specificity to two or more kinds of protein tyrosine phosphatase subunits, wherein the aforementioned fusion protein comprising a protein tyrosine phosphatase domain and another protein or a polypeptide fragment, preferably a GST-LAR phosphatase domain fusion protein, is employed as an immunogen. In this aspect of the present invention, the available another protein or a polypeptide fragment except GST to be a member of the fusion protein, and purification process of the fusion protein are as set forth above.

Further, a fusion protein comprising GST and a LAR phosphatase domain which is a preferable immunogen may be suitably produced by: culturing *Escherichia coli* transformed or transfected with an expression vector comprising a coding region of GST gene and a coding region of a phosphatase domain of LAR gene at 20–30° C. for 16–24 hours, preferably at 23–25° C. for 18 hours; and then isolating the fusion protein from the culture fluid and/or bacterial cells. Thus obtained fusion protein may also be further purified based on an affinity to a support carrying glutathione, e.g., glutathione sepharose beads, wherein the elution of the fusion protein from the glutathione sepharose beads may be performed by boiling in the presence of a detergent, as set forth above, and again, for eluting the fusion protein, the resin may be boiled at 100° C. for 5–10 minutes in the presence of the detergent at a concentration which does not lead any problems to an animal to be administered, preferably in the presence of 0.1% of sodium dodecylsulfate. Accordingly, the purified fusion protein, which is preferable as a contemplated immunogen, can be obtained.

In a method of generating a monoclonal antibody by using such a fusion protein as an immunogen, a protein tyrosine phosphatase domain, preferably a LAR phosphatase domain may be employed for screening the antibody, however, it is more preferable to perform the screening using the fusion protein that was employed as an immunogen in terms of the specificity.

Furthermore, the present invention provides a method of isolating a novel PTP comprising a step for screening PTP, wherein the aforementioned antibody is used in the step of screening. It is contemplated that expression screening of a cDNA library may be performed in the screening step.

In yet another aspect of the present invention, a method of quantitative determination of PTP and/or PTP derived molecules is provided. In this method, an amount of PTP protein and/or a fragment or a polypeptide that comprises at least a part of a PTP intracellular domain, which is contained in a test sample, is determined using the antibody set forth above. The antibody set forth above is used preferably in any of =immunoblotting, immunoprecipitation and ELISA, for determination in this method.

Still another aspect of the present invention is to provide a method for quantitative determination of PTP protein and/or PTP derived molecules comprising the steps of: isolating PTP and/or a fragment or a polypeptide that comprises at least a PTP intracellular domain from a test sample using the antibody set forth above; and measuring an activity of the isolated PTP and/or PTP derived molecules. In this step for isolation, affinity chromatography and/or immunoprecipitation by using a support that was bound with the aforementioned antibody may be suitably utilized.

In yet another aspect of the present invention, a method for producing PTP and/or PTP derived molecules is provided, comprising the step of isolating PTP protein and/or a fragment or a polypeptide that comprises at least a PTP intracellular domain using the antibody set forth above. In this step for isolation, affinity chromatography and/or immunoprecipitation by using a support that was previously bound with the antibody described above may be suitably utilized.

Further aspect contemplated by the present invention is to provide a method for identifying the presence of PTP and/or PTP derived molecules within tissue comprising the step of performing immunohistological examination using the aforementioned antibody. As the immunohistological examination, the technique such as in situ immunohistological staining with a labelled antibody may be adopted, thus PTP protein and/or a fragment or a polypeptide that comprises at least a PTP intracellular domain, can be detected.

Besides, the present inventors found that a monoclonal antibody having specific immunoreactivity with LAR can specifically recognize thyroid carcinoma cells. Therefore, the above-mentioned antibody of the present invention is presumed to be useful in diagnosis, therapy and the like of thyroid cancer.

BRIEF DESCRIPTION OF THE DRAWING

FIG. 9 represents homology of amino acid sequences of intracellular domains of LAR (SEQ ID NO: 9) and CD45 (SEQ ID NO: 10).

BEST EMBODIMENT FOR CARRYING OUT THE INVENTION

EXPERIMENTAL EXAMPLE 1

Tyrosine Phosphorylation of Insulin Receptors by LAR Mutants and Studies on Association Between LAR and Insulin Receptors First, in order to elucidate the mechanisms controlling signal transduction of insulin by LAR, analysis was performed with a strategy in which mutated LAR is used that was prepared by substitution of cysteine with serine, which exists in a catalytic center of PTP domain of LAR.

A) Expression Vector of LAR and Insulin Receptors

Figure 1A:
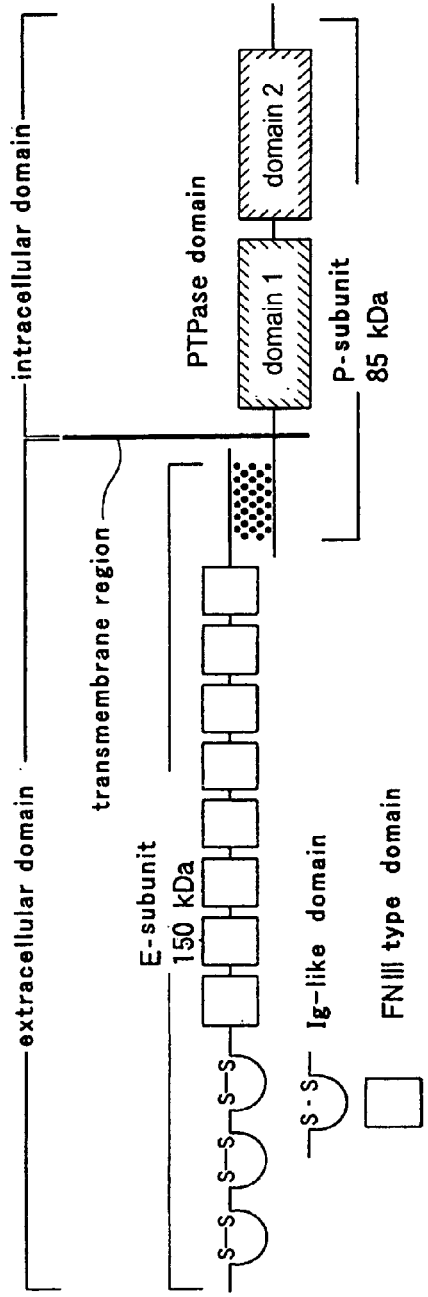
FIGS. 1A–B, FIG. 1A is a schematic drawing depicting a subunit structure of LAR (FIG. 1A) and a schematic drawing illustrating the mutated LAR phosphatase domain structures inside the membrane (FIG. 1B) prepared as demonstrated in Experimental Examples.
Figure 1B:
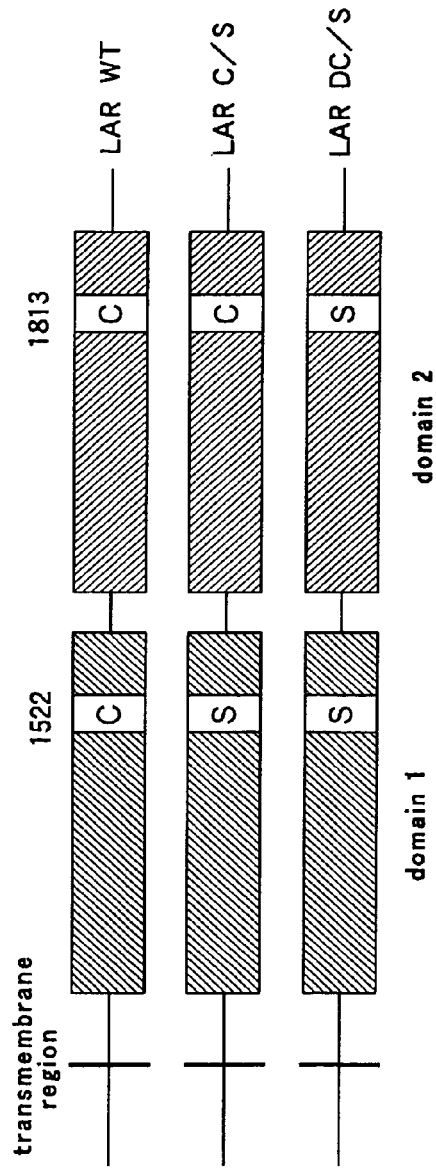

Three kinds of LAR expression vectors were used, i.e., (a) LAR WT: human wild type LAR (SEQ ID NO: 3); (b) LAR C/S: mutated LAR, having substitution of cysteine in a catalytic center of LAR-PTP domain 1 (amino acid residue position 1552 of SEQ ID NO: 3) for serine by substituting nucleotide G, position 4983 of SEQ ID NO: 3, with C; and (c) LAR DC/S: further mutated one in addition to LAR C/S, with substitution of cysteine in LAR-PTP domain 2 (amino acid residue position 1813 of SEQ ID NO: 3) for serine by substituting nucleotide G, position 5856 of SEQ ID NO: 3, with C (see, FIG. 1(b)), each of which was incorporated into pMT expression vector (see, Streuli M. et al., *EMBO J.*, 11, 897–907, 1992; and Streuli M. et al., *EMBO J.*, 9, 2399–2407, 1990).

Meanwhile, the employed insulin receptor expression vectors were: (a) IR WT: wild type; and (b) IR K1018M: mutated insulin receptor having substitution of lysine, position 1018 of ATP binding site of wild type insulin receptor, with methionine resulting in deficiency of tyrosine kinase activity, each of which cDNA was incorporated to downstream of SRα promoter (see, Kanai F. et al., *Biochemical and Biophysical Research Communications*, 195, 762–768, 1993).

B) Transfection into COS-7 Cells

COS-7 cells were seeded into RPMI 1640 medium (Nissui Pharmaceutical Co., LTD.) supplemented with 10% fetal calf serum at $1.0 \times 10^6$ cells/8 mL/90 φ dish, then after 16 hours incubation, expression vectors of LAR C/S and IR WT were cotransfected into COS-7 cells using DEAE-dextran method. The LAR C/S employed was a vector that was revealed to include complete deficiency in tyrosine phosphatase activities in vitro (Streuli M. et al., *EMBO J.*, 9, 2399–2407, 1990) according to mutation as mentioned above in paragraph A, (b).

Cotransfection was performed according to the following procedure. Initially, 40 μl of 10 mM chloroquine was added to 4 ml of RPMI 1640 medium (10.2 g/L of RPMI 1640 (Nissui Pharmaceutical Co., LTD.) containing 0.3 g of glutamine and 0.1 g of kanamycin, pH 7.4 that was adjusted with 10% $NaHCO_3$) containing 2% FCS. To 2 ml of this solution, 5 μg of LAR expression vector and 1 μg of IR expression vector were added, on the other hand, 16 μl of 100 mg/ml DEAE-dextran was added to the remaining 2 ml of the solution. Then, both solutions were mixed thoroughly with stirring. Thus prepared solution of expression vector, 3.75 ml was plated at $1.0 \times 10^6$ cells/8 ml/dish, and was added to COS-7 cells that had been precultured for 16 hours at 37° C., in a 5% $CO_2$ incubator. Following 4 hours culture under the similar conditions to the preculture, the cells were treated with 10% DMSO solution for 2 minutes, then washed with PBS (137 mM NaCl, 2.7 mM KCl, 4.3 mM $Na_2HPO_4.12H_2O$, 1.4 mM $KH_2PO_4$), thereafter, 8 ml of RPMI1640 containing 10% FCS was added thereto, and cultured for 48 hours at 37° C. in an incubator that was adjusted to 5% $CO_2$.

C) Insulin Stimulation and Preparation of Cell Lysate

COS-7 cells after completing the transfection were incubated for 16 hours in serum free RPMI 1640 culture medium, followed by stimulation with $10^{-7}$ M insulin (Seikagaku Corporation) for determined periods, i.e., 0, 1, 5, 15 and 30 minutes. Stimulation for 0 minute was conducted by standing on ice without incubating at 37° C., although insulin was added similarly. After each of the time elapsed from the beginning of insulin stimulation, culture fluid was entirely aspirated therefrom, and 5 ml of PBS w/Inh. (PBS containing tyrosine phosphatase inhibitors: 1 mM sodium vanadate, 5 mM sodium fluoride, 5 mM sodium pyrophosphate, 5 mM EDTA-2Na, 137 mM NaCl, 2.7 mM KCl, 4.3 mM $Na_2HPO_4.12H_2O$, 1.4 mM $KH_2PO_4$) was immediately added.

Following washes of the whole cells with PBS w/Inh., the fluid was removed by aspiration, and 1 ml of lysis buffer (1% Nonidet P40, 150 mM NaCl, 50 mM Tris-HCl (pH 7.4), 5 mM EDTA, 10 mM iodoacetamide, 10 mM sodium fluoride, 10 mM sodium pyrophosphate, 0.4 mM sodium vanadate, 0.1 mM oxidized phenylarsine, 1 mM benzamidine, 1 mM phenylmethylsulfonyl fluoride) was added to the cells, which were thereafter collected with a cell scraper. The cell suspension was transferred to a 1.5 ml tube, and then incubated at 4° C. for 30 minutes to effect complete lysis of the cells. Supernatant, which was obtained by centrifuge of the fluid at 12,000 rpm, 4° C. for 10 minutes following incubation was employed as a cell lysate in the experiments set forth below.

D) Immunoprecipitation

Immunoprecipitation was performed for the cell lysate obtained as above paragraph C, with an anti-LAR E-subunit antibody (a mixture of 7.5 μg of 11.1A and 7.5 μg of 75.3A, see, Streuli M. et al., *EMBO J.*, 11, 897–907, 1992). To 1 ml of the above cell lysis solution, 15 μg of MOPC 21 (mouse IgG1κ: Sigma Corporation) as a mock was added, then the solution was incubated at 4° C. for one hour, added with 20 μl of γ-bind (GammaBind Plus Sepharose: Pharmacia Biotech Inc.) thereto, and further incubated for one hour at 4° C. to execute preabsorption. The solution was centrifuged at 4° C., 12,000 rpm for 10 minutes, then 950 μl of the supernatant was transferred to another tube. Next 15 μg of anti-LAR E-subunit antibody was added to the supernatant, then the solution was incubated at 4° C. for one hour, added with 20 μl of γ-bind thereto, and further incubated for one hour at 4° C. After centrifuge at 4° C., 12,000 rpm for 10 minutes, the precipitate was washed with 1 ml of lysis buffer twice, then once with PBS w/Inh., and suspended in 20 μl of SDS sample buffer. The suspension was heated for 5 minutes in a boiling water bath to prepare a sample for electrophoresis.

E) Immunoblotting

The above-mentioned sample was subjected to electrophoresis using 7.5% SDS-polyacrylamide gel, followed by transfer to a nitrocellulose membrane (Schleicher & Schuell) using a transfer device at 400 mA for 4 hours. Then blocking was conducted by incubating the membrane in 3% bovine serum albumin solution for longer than 30 minutes at a room temperature. After washing with sufficient volume of TBS-T (TBS with Tween 20: 10 mM Tris-HCl (pH 7.4), 150 mM NaCl, 0.1% Tween 20) for 10 minutes more than twice, an anti-phosphotyrosine antibody (4G10, UBI) that was 50,000-fold diluted with TBS-T, the anti-LAR E-subunit antibody or an anti-insulin receptor β-chain antibody (UBI) was added thereto, then the mixture was shaken for one hour at a room temperature. After washing with sufficient volume of TBS-T for 5 minutes more than three times, 15 ml of TBS-T solution containing HRP-labelled anti-mouse IgG antibody (horseradish peroxidase-labelled anti-mouse IgG: Santa Cruz Biotechnology, Inc.) 1.5 ml was added thereto, and shaken for one hour at a room temperature. After washing with sufficient volume of TBS-T for 5 minutes more than three times, bands of the protein were detected that can bind to each of the antibodies, by means of a chemiluminescence method using a kit of luminescence reagents (Wako Pure Chemical Industries, Ltd.).

F) Results

Figure 2:
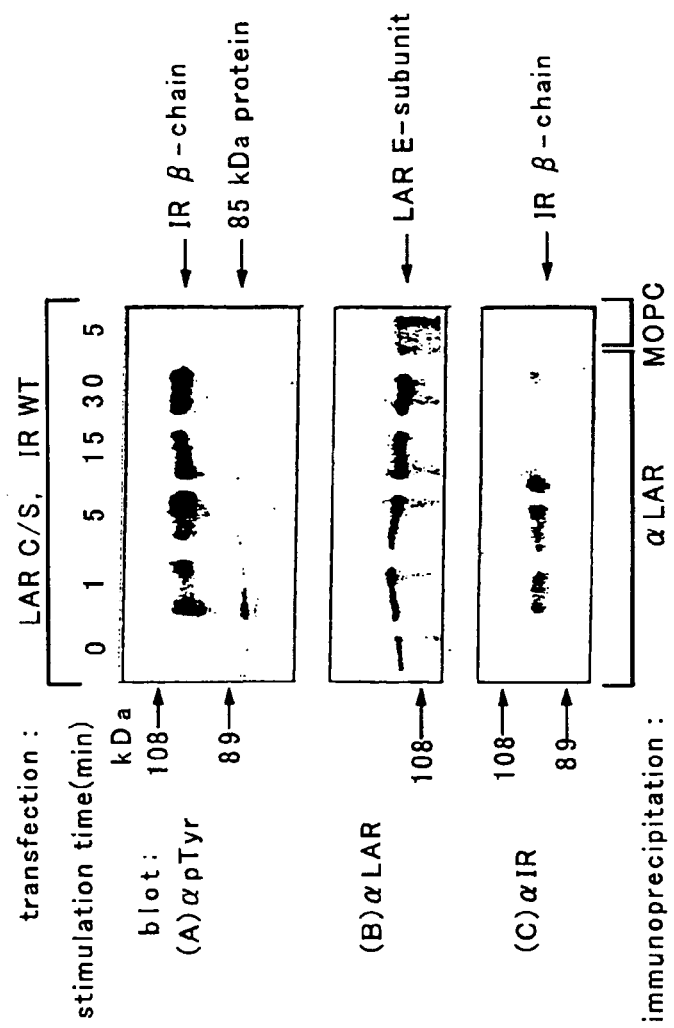
FIG. 2 represents immunoblots illustrating time dependent tyrosine phosphorylation induced by insulin stimulation in COS cells that were cotransfected with LAR/CS and wild type insulin receptor (IR).

As results of immunoblotting with the anti-phosphotyrosine antibody following to immunoprecipitation with the anti-LAR E-subunit antibody of cell lysate prepared after stimulation with insulin for determined time periods of cotransfected COS-7 cells with LAR C/S and IR WT in the above-described manner, tyrosine phosphorylation of an insulin receptor β-chain as well as a 85 kDa protein could be observed with the insulin stimulation for 1 minute. Such tyrosine phosphorylation could also be successively observed with the insulin stimulation for 30 minutes (see, FIG. 2A).

Furthermore, results from the immunoblotting with the anti-LAR E-subunit antibody (FIG. 2B), the anti-insulin receptor β-chain antibody (FIG. 2C) and the anti-phosphotyrosine antibody (FIG. 2A) demonstrated that LAR and insulin receptor may associate depending on the presence or absence of tyrosine phosphorylation of the insulin receptor.

EXPERIMENTAL EXAMPLE 2

Studies on Tyrosine Dephosphorylation of Insulin Receptor by Various LAR (1)

Next, COS-7 cells were similarly cotransfected with LAR WT, LAR C/S or LAR DC/S, and IR WT followed by stimulation with insulin for 5 minutes, and immunoprecipitation with the anti-LAR E-subunit antibody, and then immunoblotting with various types of antibodies for the precipitates was carried out. Consequently, tyrosine phosphorylation of the insulin receptor β-chain or the 85 kDa protein could not be detected for the cells cotransfected with insulin receptor and LAR WT, in comparison with the cells cotransfected with LAR C/S or LAR DC/S (see, FIG. 3A).

Additionally in these experiments, amounts of expression of LAR (FIG. 3C) and the insulin receptor (FIG. 3D) were almost identical in both of the cotransfectants, therefore LAR WT was suggested to dephosphorylate the phosphorylated tyrosine of the insulin receptor β-chain as well as the 85 kDa protein.

Figure 3:
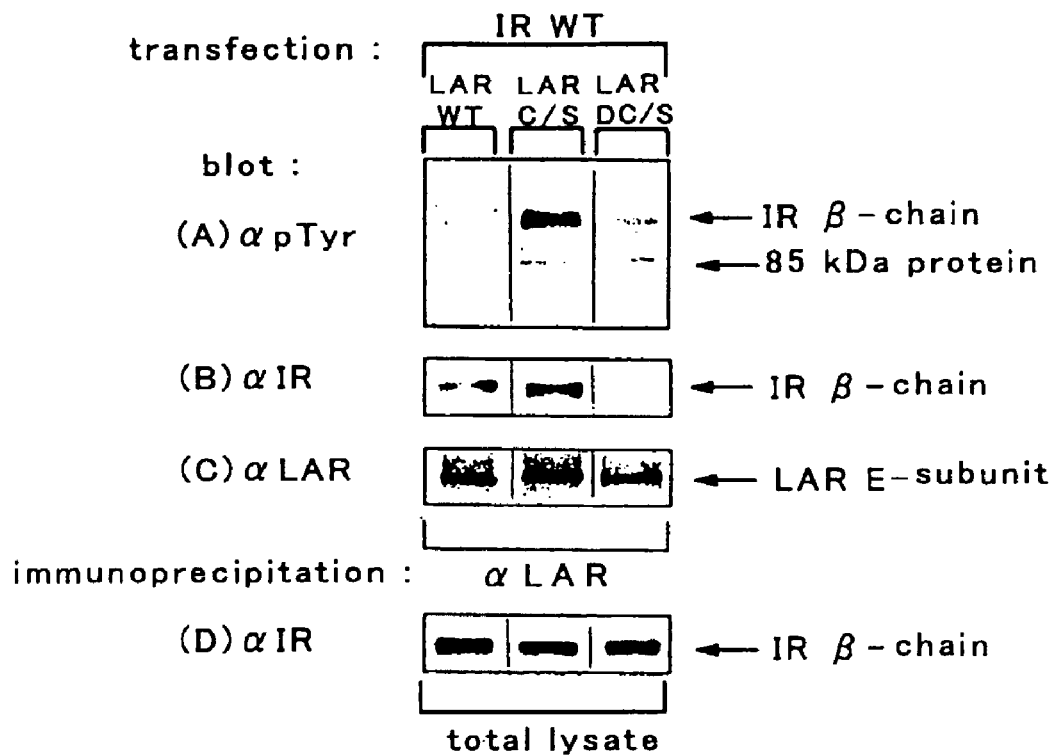
FIG. 3 represents immunoblots illustrating phosphorylation-dephosphorylation in COS cells that were cotransfected with wild type or mutants of LAR, and wild type insulin receptor.

Further, when the immunoprecipitates with the anti-LAR E-subunit antibody were immunoblotted using the anti-insulin receptor β-chain antibody, the cotransfectant with LAR DC/S showed a weaker band of an insulin receptor β-chain, compared to the cotransfectant with LAR WT or LAR C/S (FIG. 3B).

These results indicate that the association between insulin receptor and LAR DC/S is weaker, when compared with that of LAR WT or LAR C/S. The only one difference between LAR C/S and LAR DC/S is one amino acid residue position 1813 of phosphatase domain 2, accordingly, this domain 2, which was postulated to involve in binding with substrates without tyrosine phosphatase activity, was proved to be playing a role in binding between LAR and insulin receptor.

EXPERIMENTAL EXAMPLE 3

Studies on Tyrosine Dephosphorylation of Insulin Receptor by Various LAR (2)

Figure 4:
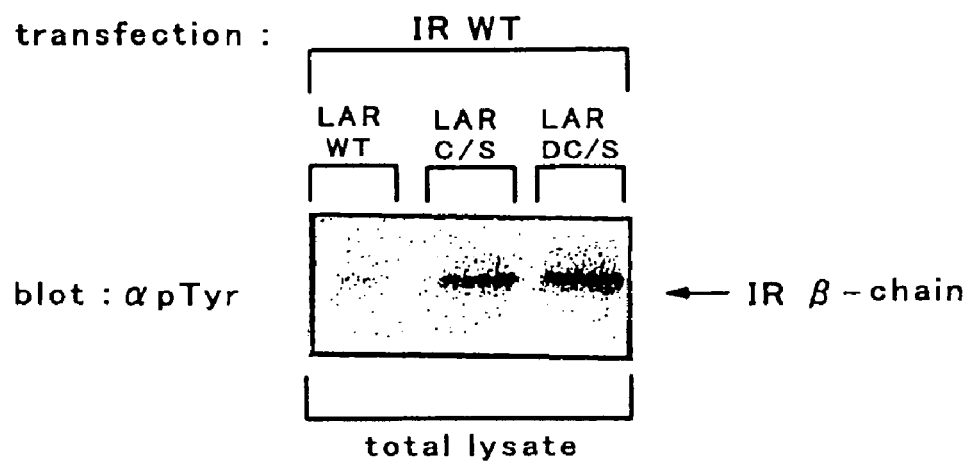
FIG. 4 represents an immunoblot illustrating dephosphorylation of a β-chain of insulin receptor by wild type or mutants of LAR.

In order to further study as to whether tyrosine dephosphorylation of insulin receptor occurs only in cases where LAR was bound, or in every insulin receptor, cell lysate of the cotransfectant was subjected to electrophoresis, and then immunoblotted with the anti-phosphotyrosine antibody. Consequently, tyrosine dephosphorylation of insulin receptor was markedly found only in cells that had been cotransfected with LAR WT (see, FIG. 4).

EXPERIMENTAL EXAMPLE 4

Figure 5:
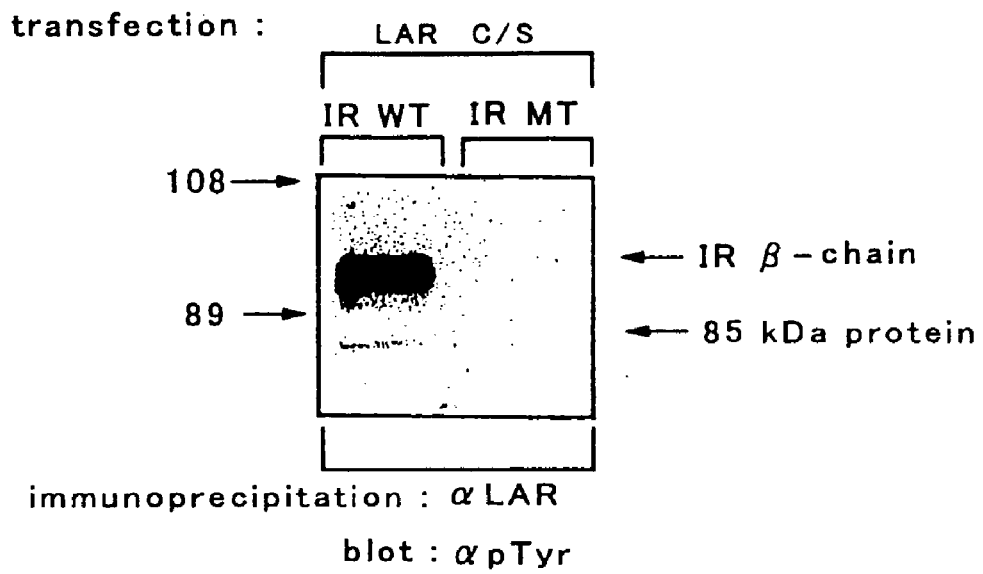
FIG. 5 represents an immunoblot illustrating tyrosine phosphorylation in COS cells that were cotransfected with wild type or mutant of insulin receptor, and LAR/CS.

Studies on Tyrosine Phosphorylation of Insulin Receptor in the Presence of LAR C/S In order to elucidate whether tyrosine phosphorylation of the 85 kDa protein is effected by a tyrosine kinase activity of insulin receptor, COS-7 cells were cotransfected with LAR C/S, and JR WT or IR K1018M(IR MT) having a deficiency in tyrosine kinase of insulin receptor. Following insulin stimulation of the cells for 5 minutes, immunoprecipitation was performed with the anti-LAR E-subunit antibody, and immunoblotting with the anti-phosphotyrosine antibody was carried out (see, FIG. 5). Consequently, the cells cotransfected with IR WT showed tyrosine phosphorylation of an insulin receptor β-chain and the 85 kDa protein upon stimulation with insulin, however, the cells cotransfected with IR K1018M showed no such phosphorylation at all.

From these results, it was revealed that rapid tyrosine phosphorylation of insulin receptor β-chain occurs upon binding of insulin to insulin receptor; and that the insulin receptor tyrosine kinase leads tyrosine phosphorylation of the 85 kDa protein.

The 85 kDa protein was therefore speculated as a P-subunit of LAR of which binding to insulin receptor was demonstrated.

EXAMPLE 1

Generation of Anti-Tyrosine Phosphatase P-Subunit Antibodies

Anti-tyrosine phosphatase P-subunit antibodies were generated according to the following procedures.

A) Preparation of Immunogen

Glutathione-S-transferase-LAR fusion protein (GST-LAR) was employed as an immunogen. $E.$ $coli$ AD202 was transformed with an expression vector, pGEX-2T vector (Pharmacia Biotech Inc.), which was incorporated to its BamHI/EcoRI site with cDNA corresponding to 607 amino acids spanning from the end of a transmembrane region of a LAR P-subunit to the entire cytoplasmic region (SEQ ID NO: 1, 3467 bp) according to a general procedure. After the $E.$ $coli$ was incubated overnight in LB (Amp. +) agar medium (LB (Amp. +) described below containing 7.5 g of agar), single colony was inoculated to 50 ml of LB (Amp. +) medium (containing triptone 10 g/L, yeast extract 5 g/L, NaCl 5 g/L, 5 N NaOH 0.2 ml/L, and ampicillin 50 μg 1 ml), and further incubated overnight. Then the incubation mixture of $E.$ $coli$ was inoculated to 500 ml of LB (Amp. +) medium, and incubated at 37° C. until absorbance at 600 nm reaches to approximately 1.0, followed by addition of 50 μl of 1 M IPTG (isopropyl-β-D(−)-thiogalactopyranoside, Wako Pure Chemical Industries, Ltd.) and an incubation at 25° C. overnight. Thus resulted culture was centrifuged at 3,000 rpm, 4° C. for 15 minutes, and the precipitated bacterial bodies were suspended in 50 ml of NETN (0.5% Nonidet P40, 1 mM EDTA, 20 mM Tris-HCl pH 8.0, 100 mM NaCl). Thereafter, the suspension was subjected to twice repeated treatments of ultrasonication for 1 minute and standing on ice for one minute, and then centrifuged at 14,000 rpm, 4° C. for 20 minutes to obtain the supernatant.

To 10 ml of the lysate of the *E. coli*, 100 μl of suspension of glutathione sepharose beads (Glutathione Sepharose 4B (Pharmacia Biotech Inc.) that had been prepared by washing three times, and suspended in 50% NETN) was added, and then incubated for 30 minutes at a room temperature. Thus resulted suspension was centrifuged at 3,000 rpm, 4° C. for 5 minutes, and supernatant was removed. The precipitated glutathione sepharose beads were washed twice with NETN, then once with PBS, thereafter 100 μl of SDS sample buffer (125 mM Tris-HCl pH 6.8, 0.1% sodium dodecylsulfate, 5% 2-mercaptoethanol) was added thereto, and heated in a boiling water bath for 10 minutes to elute the GST-LAR fusion protein. The eluate from which the beads were eliminated was concentrated by centrifuge using Centricon-10 (Amicon) at 3,000 rpm, 4° C. for 45 minutes. One ml of PBS was added to the concentrate in order to bufferize the solution, and the solution was concentrated again by centrifuge at 3,000 rpm, 4° C. for 45 minutes. This process for bufferization was repeated twice, and thus resulted solution was employed as an immunogen solution. Purification and concentration of the antigenic protein were confirmed by SDS-polyacrylamide gel electrophoresis.

Meanwhile, on a final immunization, the antigen solution was prepared in a different process because it should be administered intravenously. The lysate of the above-described *E Coli* that is expressing GST-LAR fusion protein was incubated with glutathione sepharose beads, and after centrifuge, the precipitated beads were washed twice with NETN, and three times with PBS. Next, 100 μl of GSH elution buffer (20 mM glutathione, 1 M Tris-HCl, pH 9.6) was added thereto, and the mixture was gently stirred for 10 minutes at a room temperature to accomplish the elution of GST-LAR. After repeating the steps of centrifuge at 3,000 rpm, 4° C. for 5 minutes and recovering the supernatant three times in total, the total eluate was dialyzed in saline at 4° C. for 2 days, then thus obtained solution was employed as an immunogen solution for intravenous administration.

B) Immunization

Eight female Balb/c mice of 6 weeks old received intraperitoneal administration of pristane (2,6,10,14-tetramethylpentadecane, Sigma Corporation) at 0.5 ml/animal. After 2 weeks passed, the antigen solution for intraperitoneal immunization that was emulsified by blending with Freund's complete adjuvant (Gibco Inc.) at a ratio of 1:1 was intraperitoneally administered at about 10 μg of GST-LAR fusion protein per one mouse. Thereafter, the antigen solution for intraperitoneal immunization that was admixed with Freund's incomplete adjuvant (Gibco Inc.) at a ratio of 1:1 was prepared to be about 30–70 μg of GST-LAR per one mouse, and the mixture was intraperitoneally administered four times approximately once every 2 weeks. On day 4 after the fourth immunization, blood was collected from ocular fundus vein, and an antibody titer in the serum was determined by ELISA method.

C) ELISA

Protein solutions of GST-LAR and GST alone that were prepared similarly to the procedure of preparation of the antigen for intravenous immunization were respectively dialyzed against purified water at 4° C. overnight. These solutions were adjusted to 0.5 μg/ml in PBS, and subjected to absorption to an ELISA plate (Falcon 3911 MicroTest™ Flexible Assay Plate) at 50 μl/well for one hour. After five times washes with wash buffer (PBS containing 0.05% Tween20), blocking with 5% skim milk (prepared by dissolving 2.5 g of skim milk in 50 ml of PBS) was conducted. Following washes, the serum as obtained in the above section B was diluted to 16,000 fold with dilution buffer (PBS containing 0.25% BSA), and was added to the wells at 50 μl/well, and then incubated for one hour in a wet box. After washing the plate, HRP-labelled anti-mouse IgG antibody that was diluted to 1,000 fold was added to the plate at 50 μl/well, and incubated for one hour. Following washes with wash buffer four times and once with PBS, a substrate solution of o-phenylenediamine (Wako Pure Chemical Industries, Ltd.) that was dissolved in a citrate buffer (prepared by dissolving 5.6325 g of citric acid monohydrate and 18.35 g of $Na_2HPO_4.12H_2O$ in purified water to make 500 ml in total) at a concentration of 1 mg/ml was added at 50 μl/well, allowed for reaction for 30 minutes, and then 50 μl of 10% $H_2SO_4$ was added to terminate the reaction. Fifty μl of the solution was transferred to each well of a 96-well plate (Sumitomo Bakelite Co., LTD.) for measurement, and then absorbance at 450 nm was measured.

D) Cell Fusion

Two mice that showed elevation of the antibody titer to GST-LAR in accordance with the results of the above ELISA were finally immunized by intravenous administration, and spleen was excised therefrom on the third day to prepare splenocytes according to an ordinary procedure.

Parent cells employed for cell fusion were Balb/c mouse-derived myeloma cell strain NS 1 that was previously selected in a medium containing 20 μg/ml 8-azaguanine, and confirmed as hypoxanthine, guanine, phosphoribosyl transferase (HGPRT) deficient strain. Cell fusion and cloning were performed with $2 \times 10^7$ of NS1 cells and $1 \times 10^8$ of splenocytes, using ClonaCell™-HY Hybridoma Cloning Kit (StemCell Technologies Inc.).

Screening of the supernatant from the culture of the cloned hybridoma was carried out according to ELISA method described in section C above, with 50 μl of the supernatant of hybridoma culture using plates that were bound with 0.5 μg/ml protein solution of GST, GST-LAR or GST-CD45 (Furukawa, T. et al., *Proc. Natl. Acad. Sci. USA*, 91, 10928–10932, 1994) prepared by the similar method for preparation of the antigen for intravenous immunization as described above. In this ELISA method, hybridoma was selected, which did not show any immune response to the wells bound with GST, but showed an immune response to the wells bound with GST-LAR or GST-CD45. Passage culture of the cloned hybridoma was conducted in RPMI 1640 medium (Nissui Pharmaceutical Co., LTD.) containing 10% fetal bovine serum (Gibco Inc.).

Through screening by ELISA method of the culture supernatant in this manner from the hybridoma that was HAT selected, a clone YU2 having both stable antibody producibility and proliferation ability could be obtained.

This hybridoma cell line YU2 was deposited on May 7, 1998, with National Institute of Bioscience and Human-Technology Agency of Industrial Science and Technologies, 1–3, Higashi 1 chome, Tsukuba-shi, Ibaraki-ken, 305–8566, Japan, and assigned Accession No. FERM BP-6344.

E) Typing of Monoclonal Antibody

Supernatant of 0.5 ml from culture of hybridoma YU2 obtained in the above section D was diluted with 4.5 ml of TBS-T, and the isotype was determined for 3 ml of the diluted solution using mouse monoclonal antibody isotyping kit (Amersham International plc.). As a result, the isotype of the antibody was proved to be IgG1κ.

F) Generation and Purification Of Monoclonal Antibody

Balb/c mice of 6 weeks old received intraperitoneal administration of pristane at 0.5 ml/animal, and after 10 days, hybridoma cell YU2 that was obtained by cloning in section D above was intraperitoneally injected at $2.5 \times 10^6$–$1.3 \times 10^7$ cells/0.5 ml/animal. Abdominal hypertrophy was observed approximately 10 days thereafter, accordingly, ascites fluid was collected several times using a 20-gauge injection needle. Thus collected ascites fluid was centrifuged at 1,000 rpm, 4° C. for 5 minutes to separate supernatant and precipitate. The supernatant was incubated at 37° C. for 30 minutes, and allowed to stand at 4° C. overnight. Following centrifuge at 12,000 rpm, 4° C. for 10 minutes, the monoclonal antibody YU2 was purified using an affinity column HiTrap ProteinG (Pharmacia Biotech Inc.) from the 1.5 ml of supernatant thus obtained. Absorbance at 280 nm of the antibody solution thus obtained was measured, and then concentration of the antibody was calculated using molecular extinction coefficient of mouse IgG.

Figure 6:
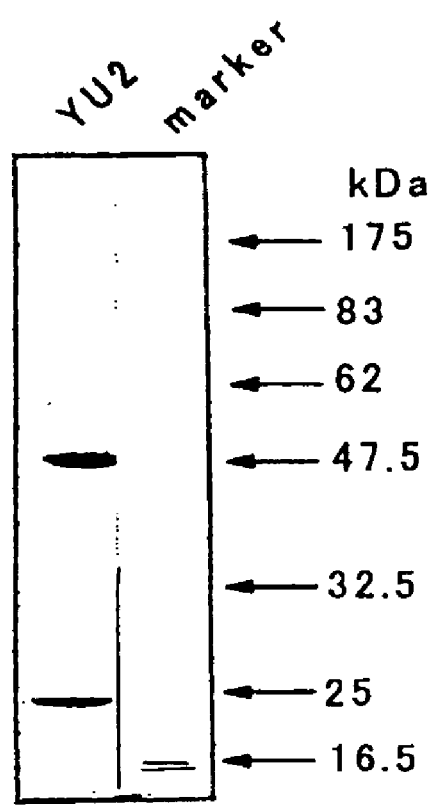
FIG. 6 represents SDS-polyacrylamide gel, showing a molecular weight of the antibody YU2 of the present invention.

In addition, a molecular weight of the monoclonal antibody YU2 was estimated from mobility on SDS-polyacrylamide gel electrophoresis. The results are shown in FIG. 6. As is clear from the FIG. 6, the monoclonal antibody YU2 comprises H-chain of about 48 kDa and L-chain of about 25 kDa, having a total molecular weight of about 146 kDa.

EXAMPLE 2

Studies On Specificity Of Monoclonal Antibody (1)

An expression vector of LAR WT was transfected into COS-7 cells according to the procedures described in Example 1, sections A and B. Following immunoprecipitation of the cell lysate with the purified monoclonal antibody obtained in Example 1, immunoblotting was carried out. As a control on immunoprecipitation, MOPC 21 was employed because the anti-LAR E-subunit antibody (supra), an anti-CD45 antibody (Santa Cruz Biotechnology, Inc., 35-Z6), and the monoclonal antibody YU2 all belong to IgG1 subclass.

Figure 7:
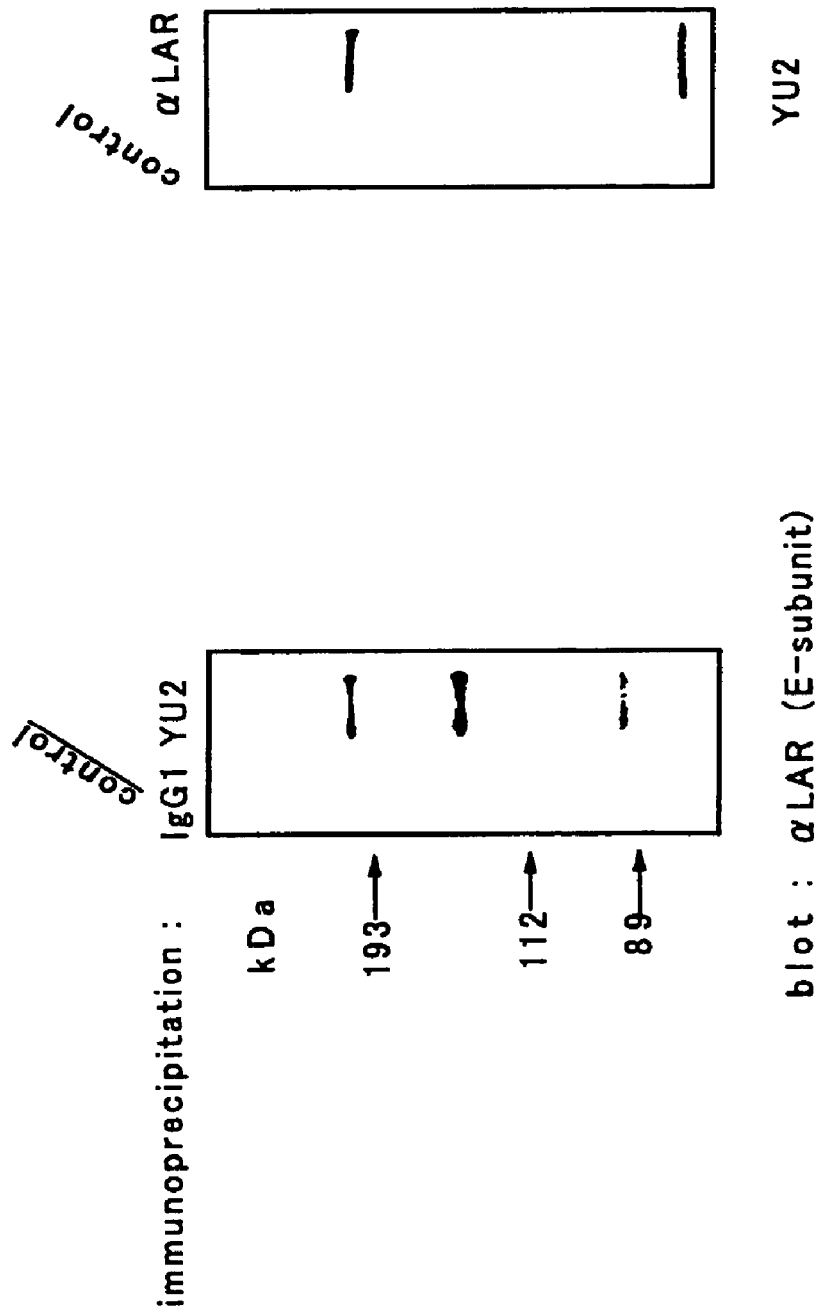
FIGS. 7A–B represent immunoblots showing immunospecificity of the antibody YU2 of the present invention.

On the analyses using the LAR enforced expression system in COS-7 cells, the monoclonal antibody YU2 recognized the protein of 85 kDa that corresponds to a LAR P-subunit and the protein of about 200 kDa that corresponds to a precursor, following immunoprecipitation with the anti-LAR E-subunit antibody (see, FIG. 7B).

Moreover, upon immunoblotting with an antibody that recognizes a LAR E-subunit after immunoprecipitation of cell extract of COS-7 cells transfected with LAR using these antibodies (IgG1, IgG2b, or YU2), detection of the protein of 150 kDa that corresponds to a LAR E-subunit and the protein of about 200 kDa that corresponds to a precursor was restricted only to that immunoprecipitated with the antibody YU2 (see, FIG. 7A).

From the results set forth above, it was revealed that the monoclonal antibody YU2 could be utilized for immunoprecipitation and immunoblotting of a LAR P-subunit.

Meanwhile, YU2 exhibited the reactivity in ELISA using GST-CD45 (Furukawa, T. et al., *Proc. Natl. Acad. Sci USA*, 91, 10928–10932, 1994) as an antigen, accordingly, it was speculated that YU2 recognized a common antigen of LAR and CD45 (presumably, a sequence in PTP domain that is conserved in both proteins) as an epitope.

EXAMPLE 3

Studies on Specificity of Monoclonal Antibody (2)

Figure 8:
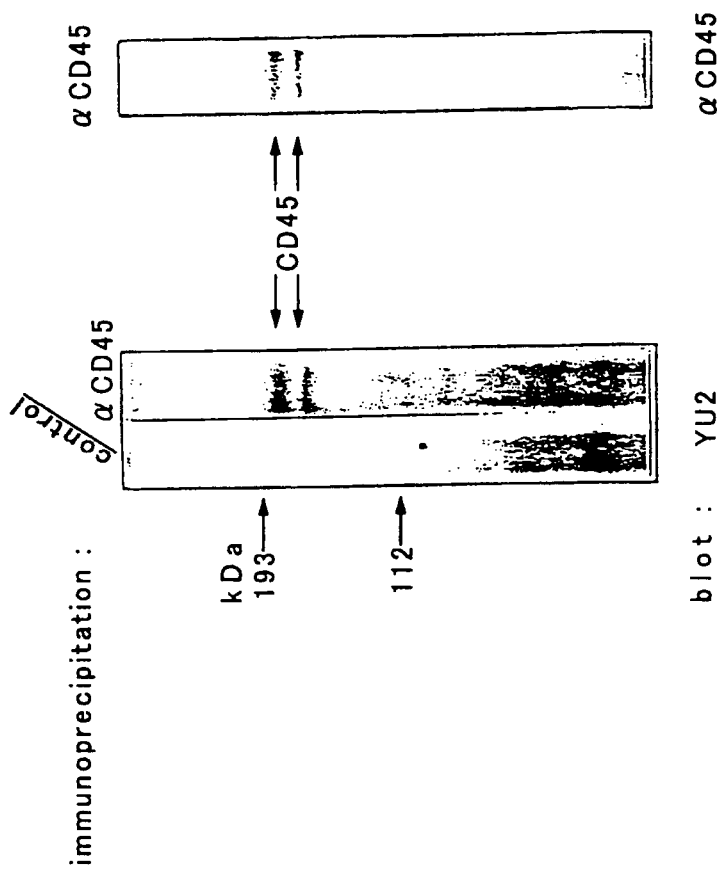
FIG. 8 represents analytical results of immunoblotting on CD45 using the antibody YU2 of the present invention.

In order to further investigate specificity of the monoclonal antibody YU2, expression of CD45 in COS-7 cells was enforced according to the similar procedure described in Experimental Example 1, thereafter the cell extract was subjected to immunoblotting analysis using YU2, and the bands were identified at positions corresponding to about 200 kDa and about 180 kDa (see, FIG. 8).

These bands were also detected at the same positions when the blot was reprobed using commercially available anti-CD45 antibody, accordingly, it was verified that these bands are derived from CD45.

From the results of the above Examples 2 and 3, it was demonstrated that YU2, which was picked up as a clone that exhibits reactivity with both of the intracellular domains of LAR and CD45 in screening of the hybridoma by means of ELISA method, can recognize CD45 also in immunoblotting.

Homology between amino acid sequences of intracellular domains of LAR (SEQ ID NO: 9) and CD45 (SEQ ID NO: 10) is shown in FIG. 9. In the figure, "*" denotes the identical amino acid, whereas "." denotes the similar amino acid between both amino acid sequences. When the amino acid sequences from the phosphatase domain 1 to C-terminal end in the intracellular domains of LAR and CD45 are compared, it was revealed that the homology was 39.4%. Among them, 12 amino acids corresponding to the vicinity of consensus sequence that carries tyrosine phosphatase activity in domain 1 (Val-Val-His-Cys-Ser-Ala-Gly-Val-Gly-Arg-Thr-Gly; SEQ ID NO: 4 (amino acids from position 245 to 256 in SEQ ID NO: 1) are completely identical (the portion depicted with outline characters in FIG. 9). It is reported that a polypeptide must include approximately 8 to 10 amino acids in order to be a possible antigen determinant, therefore, it is expected that YU2 may recognize the consensus sequence of the phosphatase comprising the 12 amino acids set out in SEQ ID NO: 4 as an epitope.

In FIG. 9, eight sites corresponding to the portions of consensus sequences in the intracellular domains of LAR and CD45 with other known PTPs (namely, PTPα, β, γ, δ, ε, σ, μ, κ, η, ζ and the like) are depicted with closed boxes. These consensus sequences in the eight sites are repetitive sequences of four kinds of sequences ((1) to (4) in FIG. 9) of which details are as follows:

(1) Phe-Trp-(Arg/Glu/Leu)-Met-(Val/Ile/Cys)-Trp (SEQ ID NO: 5)
(2) Lys-Cys-(Ala/Asp)-(Gln/Glu/Lys)-Tyr-Trp-Pro (SEQ ID NO: 6)
(3) Trp-Pro-Asp-(His/Phe)-Gly-Val (SEQ ID NO: 7)
(4) Pro-Xaa-(Ile/Val)-(Ile/Val)-His-Cys-Xaa-Ala-Gly-Xaa-Gly-Arg-(Thr/Ser)-Gly (SEQ ID NO: 8)

The above-mentioned identical sequences of LAR and CD45 set out in SEQ ID NO: 4 are included in the consensus sequence (4) in domain 1. It is expected that the antibody of the present invention that can recognize such a consensus sequence of PTP as an epitope can be utilized advantageously in analysis and quantitative determination of PTPs, identification, detection, isolation and purification of novel PTPs.

Figure 10:
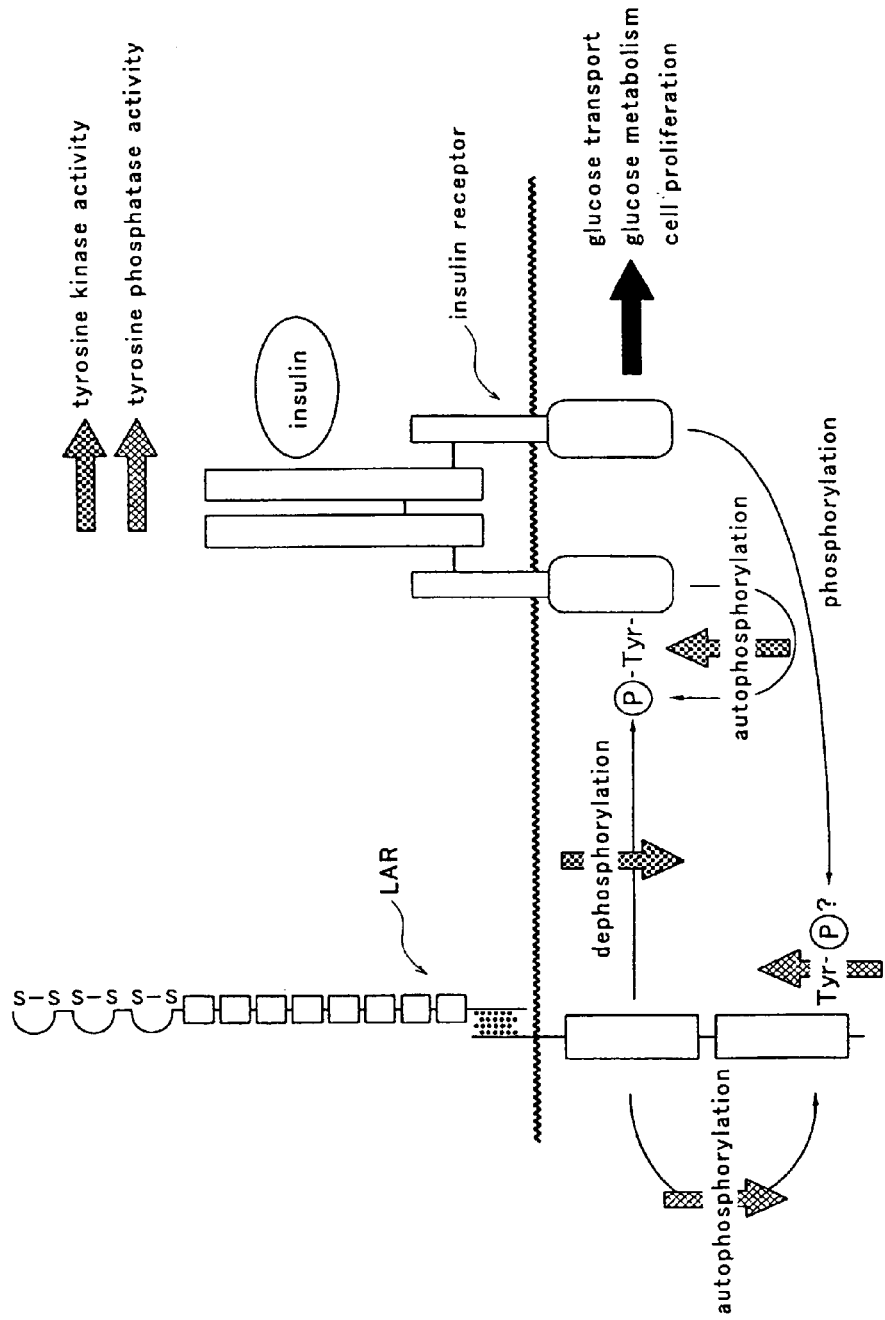
FIG. 10 is a schematic drawing depicting a signal transduction cascade of insulin that is controlled by phosphorylation-dephosphorylation in which insulin receptor and LAR participate.

In addition, as is shown in FIG. 10, tyrosine kinase activity is increased upon autophosphorylation of the β-chain of insulin receptor when insulin is bound to the α-chain of the insulin receptor. Due to the activity of the tyrosine kinase, insulin actions such as glucose uptake, glucose metabolism, and cell proliferation may be finally achieved. The present inventors clarified that the activated insulin receptor may change back into the inactivated state through tyrosine dephosphorylation by LAR (see, International Application PCT/JP98/02542, filed on Jun. 5, 1998). Moreover, the possibilities were suggested that: (1) insulin receptor tyrosine kinase may phospholylate tyrosine in intracellular domain of LAR; (2) such phosphorylation may participate in determination of substrate specificity of LAR or in increase of phosphatase activity; and (3) LAR may control its own enzymatic activity through autodephosphorylation of the phosphorylated tyrosine, accordingly, it was demonstrated at the molecular level that acceleration of the enzymatic activity of LAR may cause insulin resistance. According to the antibody of the present invention, elucidation of signal transduction mechanisms and various other control mechanisms in which phosphorylation and/or dephosphorylation may participate can be achieved, where LAR and CD45 as well as other PTPs may be involved.

INDUSTRIAL APPLICABILITY

The antibodies to intracellular domains of PTPs that are provided by the present invention can bind to an intracellular domain of LAR, or both intracellular domains of CD45 and LAR. These antibodies of the present invention are believed to recognize consensus sequence(s) of phosphatase domains of PTPs, therefore, they are useful for analysis and quantitation of PTPs, for identification and detection of novel PTPs, and for obtaining novel phosphatases by cloning and the like. Furthermore, these antibodies can be extremely useful tools for elucidating signal transduction mechanisms of insulin, and various control mechanisms. Furthermore, the antibodies can be applied for developing useful diagnostic methods of insulin resistance and NIDDM, for prophylaxis and diagnosis of various disease states of syndrome X that is based on insulin resistance, and for prophylaxis and diagnosis of onsets of arteriosclerosis and cardiac diseases.

What is claimed is:

1. A monoclonal antibody having specificity to both an intracellular domain of LAR and an intracellular domain of CD45.

2. The antibody according to claim 1 having specificity to phosphatase domains of protein tyrosine phosphatases.

3. The antibody according to claim 1, which is generated using a polypeptide that is encoded by a nucleotide sequence set forth in SEQ ID NO: 1.

4. The antibody according to claim 1 wherein the antibody is generated using a GST-LAR phosphatase domain fusion protein as an immunogen.

5. The antibody according to claim 4 wherein the GST-LAR phosphatase domain fusion protein is produced by: culturing Escherichia coli transformed or transfected with an expression vector comprising a coding region of GST gene and a coding region of a phosphatase domain of LAR gene at 20–30° C. for 16–24 hours; and isolating the fusion protein from the culture fluid and/or bacterial cells.

6. The antibody according to claim 5 wherein the GST-LAR phosphatase domain fission protein is further purified based on an affinity to a support carrying glutathione, and the elution of said fusion protein from the support is performed by boiling in the presence of a detergent.

7. The antibody according to claim 4 wherein screening of the antibody that was generated using the GST-LAR phosphatase domain fusion protein as an immunogen is performed using said fusion protein.

8. A monoclonal antibody having specificity to an intracellular domain of a protein tyrosine phosphatase, which is produced by a hybridoma with Accession No. FERM BP-6344.

9. The antibody according to claim 1 having a molecular weight of about 146 kDA.

10. A hybridoma cell line that produces the monoclonal antibody according to claim 1.

11. A hybridoma cell line with Accession No. FERM BP-6344.

12. A method for generating an antibody according to claim 1, comprising the step of:

immunizing an animal with a GST-LAR phosphatase domain fusion protein;

preparing a hybridoma cell line from an antibody-producing cell obtained from the immunized animal; and producing a monoclonal antibody from the hybridoma cell line.

13. The method according to claim 12 wherein the GST-LAR phosphatase domain fusion protein is produced by: culturing Escherichia coli transformed or transfected with an expression vector comprising a coding region of GST gene and a coding region of a phosphatase domain of LAR gene at 20–30° C. for 16–24 hours; and isolating the fusion protein from the culture fluid and/or bacterial cells.

14. The method according to claim 13 wherein the GST-LAR phosphatase domain fusion protein is further purified based on an affinity to a support carrying glutathione, and the elution of said fusion protein from the support is performed by boiling in the presence of a detergent.

15. The method according to claim 12, further comprising the step of:

screening antibodies generated in the producing step using said GST-LAR phosphatase domain fusion protein.

* * * * *

UNITED STATES PATENT AND TRADEMARK OFFICE
CERTIFICATE OF CORRECTION

PATENT NO. : 6,933,135 B1  Page 1 of 1
APPLICATION NO. : 09/743492
DATED : August 23, 2005
INVENTOR(S) : Hiroshi Yamamoto et al.

It is certified that error appears in the above-identified patent and that said Letters Patent is hereby corrected as shown below:

On the Title Page:

At item (75), 1st Inventor, "Toyonaka" should be -- Osaka --.

At item (75), 2nd Inventor, "Kawanishi" should be -- Hyogo --.

In the Claims:

At Column 49, line 46, "fission" should be -- fusion --.

Signed and Sealed this

Twenty-sixth Day of February, 2008

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 3467
<212> TYPE: DNA
<213> ORGANISM: Homo sapiens
<220> FEATURE:
<221> NAME/KEY: CDS
<222> LOCATION: (6)..(1826)
<220> FEATURE:
<221> NAME/KEY: misc_feature
<222> LOCATION: (213)..(953)
<223> OTHER INFORMATION: Tyrosine Phosphatase Domain 1
<220> FEATURE:
<221> NAME/KEY: misc_feature
<222> LOCATION: (1080)..(1826)
<223> OTHER INFORMATION: Tyrosine Phosphatase Domain 2
<220> FEATURE:
<223> OTHER INFORMATION: Description of Unknown Organism: Signature
      Motif Conserved in Phosphatase Domain of Known PTPs.
<300> PUBLICATION INFORMATION:
<308> DATABASE ACCESSION NUMBER: DDBJ/EMBL/GenBank Accession No. Y00815
<309> DATABASE ENTRY DATE: 1995-09-19

<400> SEQUENCE: 1 gatcc gga ctg aag gac tcc ttg ctg gcc cac tcc tct gac cct gtg gag      50
      Gly Leu Lys Asp Ser Leu Leu Ala His Ser Ser Asp Pro Val Glu
        1               5                  10                  15 atg cgg agg ctc aac tac cag acc cca ggt atg cga gac cac cca ccc        98
Met Arg Arg Leu Asn Tyr Gln Thr Pro Gly Met Arg Asp His Pro Pro
                 20                  25                  30 atc ccc atc acc gac ctg gcg gac aac atc gag cgc ctc aaa gcc aac       146
Ile Pro Ile Thr Asp Leu Ala Asp Asn Ile Glu Arg Leu Lys Ala Asn
             35                  40                  45 gat ggc ctc aag ttc tcc cag gag tat gag tcc atc gac cct gga cag       194
Asp Gly Leu Lys Phe Ser Gln Glu Tyr Glu Ser Ile Asp Pro Gly Gln
         50                  55                  60 cag ttc acg tgg gag aat tca aac ctg gag gtg aac aag ccc aag aac       242
Gln Phe Thr Trp Glu Asn Ser Asn Leu Glu Val Asn Lys Pro Lys Asn
     65                  70                  75 cgc tat gcg aat gtc atc gcc tac gac cac tct cga gtc atc ctt acc       290
Arg Tyr Ala Asn Val Ile Ala Tyr Asp His Ser Arg Val Ile Leu Thr
 80                  85                  90                  95 tct atc gat ggc gtc ccc ggg agt gac tac atc aat gcc aac tac atc       338
Ser Ile Asp Gly Val Pro Gly Ser Asp Tyr Ile Asn Ala Asn Tyr Ile
                100                 105                 110 gat ggc tac cgc aag cag aat gcc tac atc gcc acg cag ggc ccc ctg       386
Asp Gly Tyr Arg Lys Gln Asn Ala Tyr Ile Ala Thr Gln Gly Pro Leu
            115                 120                 125 ccc gag acc atg ggc gat ttc tgg aga atg gtg tgg gaa cag cgc acg       434
```

-continued

```
                Pro Glu Thr Met Gly Asp Phe Trp Arg Met Val Trp Glu Gln Arg Thr
                            130                 135                 140 gcc act gtg gtc atg atg aca cgg ctg gag gag aag tcc cgg gta aaa              482
Ala Thr Val Val Met Met Thr Arg Leu Glu Glu Lys Ser Arg Val Lys
    145                 150                 155 tgt gat cag tac tgg cca gcc cgt ggc acc gag acc tgt ggc ctt att              530
Cys Asp Gln Tyr Trp Pro Ala Arg Gly Thr Glu Thr Cys Gly Leu Ile
160                 165                 170                 175 cag gtg acc ctg ttg gac aca gtg gag ctg gcc aca tac act gtg cgc              578
Gln Val Thr Leu Leu Asp Thr Val Glu Leu Ala Thr Tyr Thr Val Arg
                180                 185                 190 acc ttc gca ctc cac aag agt ggc tcc agt gag aag cgt gag ctg cgt              626
Thr Phe Ala Leu His Lys Ser Gly Ser Ser Glu Lys Arg Glu Leu Arg
            195                 200                 205 cag ttt cag ttc atg gcc tgg cca gac cat gga gtt cct gag tac cca              674
Gln Phe Gln Phe Met Ala Trp Pro Asp His Gly Val Pro Glu Tyr Pro
        210                 215                 220 act ccc atc ctg gcc ttc cta cga cgg gtc aag gcc tgc aac ccc cta              722
Thr Pro Ile Leu Ala Phe Leu Arg Arg Val Lys Ala Cys Asn Pro Leu
    225                 230                 235 gac gca ggg ccc atg gtg gtg cac tgc agc gcg ggc gtg ggc cgc acc              770
Asp Ala Gly Pro Met Val Val His Cys Ser Ala Gly Val Gly Arg Thr
240                 245                 250                 255 ggc tgc ttc atc gtg att gat gcc atg ttg gag cgg atg aag cac gag              818
Gly Cys Phe Ile Val Ile Asp Ala Met Leu Glu Arg Met Lys His Glu
                260                 265                 270 aag acg gtg gac atc tat ggc cac gtg acc tgc atg cga tca cag agg              866
Lys Thr Val Asp Ile Tyr Gly His Val Thr Cys Met Arg Ser Gln Arg
            275                 280                 285 aac tac atg gtg cag acg gag gac cag tac gtg ttc atc cat gag gcg              914
Asn Tyr Met Val Gln Thr Glu Asp Gln Tyr Val Phe Ile His Glu Ala
        290                 295                 300 ctg ctg gag gct gcc acg tgc ggc cac aca gag gtg cct gcc cgc aac              962
Leu Leu Glu Ala Ala Thr Cys Gly His Thr Glu Val Pro Ala Arg Asn
    305                 310                 315 ctg tat gcc cac atc cag aag ctg ggc caa gtg cct cca ggg gag agt             1010
Leu Tyr Ala His Ile Gln Lys Leu Gly Gln Val Pro Pro Gly Glu Ser
320                 325                 330                 335 gtg acc gcc atg gag ctc gag ttc aag ttg ctg gcc agc tcc aag gcc             1058
Val Thr Ala Met Glu Leu Glu Phe Lys Leu Leu Ala Ser Ser Lys Ala
                340                 345                 350 cac acg tcc cgc ttc atc agc gcc aac ctg ccc tgc aac aag ttc aag             1106
His Thr Ser Arg Phe Ile Ser Ala Asn Leu Pro Cys Asn Lys Phe Lys
            355                 360                 365 aac cgg ctg gtg aac atc atg ccc tac gaa ttg acc cgt gtg tgt ctg             1154
Asn Arg Leu Val Asn Ile Met Pro Tyr Glu Leu Thr Arg Val Cys Leu
        370                 375                 380 cag ccc atc cgt ggt gtg gag ggc tct gac tac atc aat gcc agc ttc             1202
Gln Pro Ile Arg Gly Val Glu Gly Ser Asp Tyr Ile Asn Ala Ser Phe
    385                 390                 395 ctg gat ggt tat aga cag cag aag gcc tac ata gct aca cag ggg cct             1250
Leu Asp Gly Tyr Arg Gln Gln Lys Ala Tyr Ile Ala Thr Gln Gly Pro
400                 405                 410                 415 ctg gca gag agc acc gag gac ttc tgg cgc atg cta tgg gag cac aat             1298
Leu Ala Glu Ser Thr Glu Asp Phe Trp Arg Met Leu Trp Glu His Asn
                420                 425                 430 tcc acc atc atc gtc atg ctg acc aag ctt cgg gag atg ggc agg gag             1346
Ser Thr Ile Ile Val Met Leu Thr Lys Leu Arg Glu Met Gly Arg Glu
            435                 440                 445
```

-continued

| | | |
|---|---|---|
| aaa tgc cac cag tac tgg cca gca gag cgc tct gct cgc tac cag tac<br>Lys Cys His Gln Tyr Trp Pro Ala Glu Arg Ser Ala Arg Tyr Gln Tyr<br>                        450                        455                     460 | 1394 |
| ttt gtt gtt gac ccg atg gct gag tac aac atg ccc cag tat atc ctg<br>Phe Val Val Asp Pro Met Ala Glu Tyr Asn Met Pro Gln Tyr Ile Leu<br>465                        470                        475 | 1442 |
| cgt gag ttc aag gtc acg gat gcc cgg gat ggg cag tca agg aca atc<br>Arg Glu Phe Lys Val Thr Asp Ala Arg Asp Gly Gln Ser Arg Thr Ile<br>480                        485                        490                     495 | 1490 |
| cgg cag ttc cag ttc aca gac tgg cca gag cag ggc gtg ccc aag aca<br>Arg Gln Phe Gln Phe Thr Asp Trp Pro Glu Gln Gly Val Pro Lys Thr<br>                        500                        505                     510 | 1538 |
| ggc gag gga ttc att gac ttc atc ggg cag gtg cat aag acc aag gag<br>Gly Glu Gly Phe Ile Asp Phe Ile Gly Gln Val His Lys Thr Lys Glu<br>               515                        520                     525 | 1586 |
| cag ttt gga cag gat ggg cct atc acg gtg cac tgc agt gct ggc gtg<br>Gln Phe Gly Gln Asp Gly Pro Ile Thr Val His Cys Ser Ala Gly Val<br>                        530                        535                     540 | 1634 |
| ggc cgc acc ggg gtg ttc atc act ctg agc atc gtc ctg gag cgc atg<br>Gly Arg Thr Gly Val Phe Ile Thr Leu Ser Ile Val Leu Glu Arg Met<br>545                        550                        555 | 1682 |
| cgc tat gag ggc gtg gtc gac atg ttt cag acc gtg aag acc ctg cgt<br>Arg Tyr Glu Gly Val Val Asp Met Phe Gln Thr Val Lys Thr Leu Arg<br>560                        565                        570                     575 | 1730 |
| aca cag cgt cct gcc atg gtg cag aca gag gac cag tat cag ctg tgc<br>Thr Gln Arg Pro Ala Met Val Gln Thr Glu Asp Gln Tyr Gln Leu Cys<br>                        580                        585                     590 | 1778 |
| tac cgt gcg gcc ctg gag tac ctc ggc agc ttt gac cac tat gca acg<br>Tyr Arg Ala Ala Leu Glu Tyr Leu Gly Ser Phe Asp His Tyr Ala Thr<br>               595                        600                     605 | 1826 |
| taactaccgc tcccctctcc tccgccaccc ccgccgtggg gctccggagg ggacccagct | 1886 |
| cctctgagcc ataccgacca tcgtccagcc ctcctacgca gatgctgtca ctggcagagc | 1946 |
| acagcccacg gggatcacag cgtttcagga acgttgccac accaatcaga gagcctagaa | 2006 |
| catccctggg caagtggatg gcccagcagg caggcactgt ggcccttctg tccaccagac | 2066 |
| ccacctggag cccgcttcaa gctctctgtt gcgctcccgc atttctcatg cttcttctca | 2126 |
| tggggtgggg ttgggcaaa gcctcctttt taatacatta agtgggtag actgagggat | 2186 |
| tttagcctct tccctctgat ttttcctttc gcgaatccgt atctgcagaa tgggccactg | 2246 |
| tagggttgg ggtttatttt gttttgtttt ttttttttt ttgtatgact tctgctgaag | 2306 |
| gacagaacat tgccttcctc gtgcagagct ggggctgcca gcctgagcgg aggctcggcc | 2366 |
| gtgggccggg aggcagtgct gatccggctg ctcctccagc ccttcagacg agatcctgtt | 2426 |
| tcagctaaat gcagggaaac tcaatgtttt tttaagtttt gttttccctt taaagccttt | 2486 |
| ttttaggcca cattgacagt ggtgggcggg gagaagatag ggaacactca tccctggtcg | 2546 |
| tctatcccag tgtgtgttta acattcacag cccagaacca cagatgtgtc tgggagagcc | 2606 |
| tggcaaggca ttcctcatca ccatcgtgtt tgcaaaggtt aaaacaaaaa caaaaaacca | 2666 |
| caaaataaa aacaaaaaa aacaaaaaac ccaaaaaaaa aaaaaaaaag agtcagccct | 2726 |
| tggcttctgc ttcaaaccct caagagggga agcaactccg tgtgcctggg gttcccgagg | 2786 |
| gagctgctgg ctgacctggg cccacagagc ctggctttgg tccccagcat tgcagtatgg | 2846 |
| tgtggtgttt gtaggctgtg gggtctggct gtgtggccaa ggtgaatagc acaggttagg | 2906 |
| gtgtgtgcca cacccatgc acctcagggc caagcggggg cgtggctggc ctttcaggtc | 2966 |
| caggccagtg ggcctggtag cacatgtctg tcctcagagc aggggccaga tgattttcct | 3026 |

-continued

```
ccctggtttg cagctgtttt caaagccccc gataatcgct cttttccact ccaagatgcc      3086
ctcataaacc aatgtggcaa gactactgga cttctatcaa tggtactcta atcagtcctt      3146
attatcccag cttgctgagg ggcagggaga gcgcctcttc ctctgggcag cgctatctag      3206
ataggtaagt gggggcgggg aagggtgcat agctgtttta gctgagggac gtggtgccga      3266
cgtccccaaa cctagctagg ctaagtcaag atcaacattc cagggttggt aatgttggat      3326
gatgaaacat tcatttttac cttgtggatg ctagtgctgt agagttcact gttgtacaca      3386
gtctgttttc tatttgttaa gaaaaactac agcatcattg cataattctt gatggtaata      3446
aatttgaata atcagatttc t                                                3467
```

```
<210> SEQ ID NO 2
<211> LENGTH: 11
<212> TYPE: PRT
<213> ORGANISM: Artificial sequence
<220> FEATURE:
<223> OTHER INFORMATION: Description of Unknown Organism: Signature
      Motif Conserved in Phosphatase Domain of Known PTPs.
<220> FEATURE:
<221> NAME/KEY: SITE
<222> LOCATION: (1)
<223> OTHER INFORMATION: Xaa = Ile or Val
<220> FEATURE:
<221> NAME/KEY: SITE
<222> LOCATION: (10)
<223> OTHER INFORMATION: Xaa= Ser or Thr
<220> FEATURE:
<221> NAME/KEY: SITE
<222> LOCATION: (4)
<223> OTHER INFORMATION: Xaa= Unknown
<220> FEATURE:
<221> NAME/KEY: SITE
<222> LOCATION: (7)..(8)
<223> OTHER INFORMATION: Xaa= Unknown

<400> SEQUENCE: 2

Xaa His Cys Xaa Ala Gly Xaa Xaa Arg Xaa Gly
  1               5                  10
```

```
<210> SEQ ID NO 3
<211> LENGTH: 7702
<212> TYPE: DNA
<213> ORGANISM: Homo sapiens
<220> FEATURE:
<221> NAME/KEY: CDS
<222> LOCATION: (371)..(6061)
<220> FEATURE:
<221> NAME/KEY: sig_peptide
<222> LOCATION: (371)..(418)
<220> FEATURE:
<221> NAME/KEY: mat_peptide
<222> LOCATION: (419)..(6061)
<220> FEATURE:
<221> NAME/KEY: misc_feature
<222> LOCATION: (419)..(4120)
<223> OTHER INFORMATION: Extracellular Domain
<220> FEATURE:
<221> NAME/KEY: misc_feature
<222> LOCATION: (4121)..(4192)
<223> OTHER INFORMATION: Transmembrane Domain
<220> FEATURE:
<221> NAME/KEY: misc_feature
<222> LOCATION: (4193)..(6061)
<223> OTHER INFORMATION: Cytoplasmic Domain
<300> PUBLICATION INFORMATION:
<308> DATABASE ACCESSION NUMBER: DDBJ/EMBL/GenBank Accession No. Y00815
<309> DATABASE ENTRY DATE: 1995-09-19

<400> SEQUENCE: 3
```

```
cgggagcggc gggagcggtg gcggcggcag aggcggcggc tccagcttcg gctccggctc    60
gggctcgggc tccggctccg gctccggctc cggctccagc tcggtggcg gtggcgggag    120 cgggaccagg tggaggcggc ggcggcagag gagtgggagc agcggcccta gcggcttgcg   180
gggggacatg cggaccgacg gccccctggat aggcggaagg agtggaggcc ctggtgcccg   240
gcccttggtg ctgagtatcc agcaagagtg accgggtga agaagcaaag actcggttga    300
ttgtcctggg ctgtggctgg ctgtggagct agagccctgg atggcccctg agccagcccc   360
agggaggacg atg gtg ccc ctt gtg cct gca ctg gtg atg ctt ggt ttg     409
           Met Val Pro Leu Val Pro Ala Leu Val Met Leu Gly Leu
                -15              -10              -5 gtg gca ggc gcc cat ggt gac agc aaa cct gtc ttc att aaa gtc cct    457
Val Ala Gly Ala His Gly Asp Ser Lys Pro Val Phe Ile Lys Val Pro
         -1   1               5                   10 gag gac cag act ggg ctg tca gga ggg gta gcc tcc ttc gtg tgc caa    505
Glu Asp Gln Thr Gly Leu Ser Gly Gly Val Ala Ser Phe Val Cys Gln
     15              20                  25 gct aca gga gaa ccc aag ccg cgc atc aca tgg atg aag aag ggg aag    553
Ala Thr Gly Glu Pro Lys Pro Arg Ile Thr Trp Met Lys Lys Gly Lys
 30              35                  40                  45 aaa gtc agc tcc cag cgc ttc gag gtc att gag ttt gat gat ggg gca    601
Lys Val Ser Ser Gln Arg Phe Glu Val Ile Glu Phe Asp Asp Gly Ala
             50                  55                  60 ggg tca gtg ctt cgg atc cag cca ttg cgg gtg cag cga gat gaa gcc    649
Gly Ser Val Leu Arg Ile Gln Pro Leu Arg Val Gln Arg Asp Glu Ala
             65                  70                  75 atc tat gag tgt aca gct act aac agc ctg ggt gag atc aac act agt    697
Ile Tyr Glu Cys Thr Ala Thr Asn Ser Leu Gly Glu Ile Asn Thr Ser
         80                  85                  90 gcc aag ctc tca gtg ctc gaa gag gaa cag ctg ccc cct ggg ttc cct    745
Ala Lys Leu Ser Val Leu Glu Glu Glu Gln Leu Pro Pro Gly Phe Pro
     95                 100                 105 tcc atc gac atg ggg cct cag ctg aag gtg gtg gag aag gca cgc aca    793
Ser Ile Asp Met Gly Pro Gln Leu Lys Val Val Glu Lys Ala Arg Thr
110                 115                 120                 125 gcc acc atg cta tgt gcc gca ggc gga aat cca gac cct gag att tct    841
Ala Thr Met Leu Cys Ala Ala Gly Gly Asn Pro Asp Pro Glu Ile Ser
                130                 135                 140 tgg ttc aag gac ttc ctt cct gta gac cct gcc acg agc aac ggc cgc    889
Trp Phe Lys Asp Phe Leu Pro Val Asp Pro Ala Thr Ser Asn Gly Arg
            145                 150                 155 atc aag cag ctg cgt tca ggt gcc ttg cag ata gag agc agt gag gaa    937
Ile Lys Gln Leu Arg Ser Gly Ala Leu Gln Ile Glu Ser Ser Glu Glu
            160                 165                 170 tcc gac caa ggc aag tac gag tgt gtg gcg acc aac tcg gca ggc aca    985
Ser Asp Gln Gly Lys Tyr Glu Cys Val Ala Thr Asn Ser Ala Gly Thr
175                 180                 185 cgt tac tca gcc cct gcg aac ctg tat gtg cga gtg cgc cgc gtg gct    1033
Arg Tyr Ser Ala Pro Ala Asn Leu Tyr Val Arg Val Arg Arg Val Ala
190                 195                 200                 205 cct cgt ttc tcc atc cct ccc agc agc cag gag gtg atg cca ggc ggc    1081
Pro Arg Phe Ser Ile Pro Pro Ser Ser Gln Glu Val Met Pro Gly Gly
                210                 215                 220 agc gtg aac ctg aca tgc gtg gca gtg ggt gca ccc atg ccc tac gtg    1129
Ser Val Asn Leu Thr Cys Val Ala Val Gly Ala Pro Met Pro Tyr Val
            225                 230                 235 aag tgg atg atg ggg gcc gag gag ctc acc aag gag gat gag atg cca    1177
Lys Trp Met Met Gly Ala Glu Glu Leu Thr Lys Glu Asp Glu Met Pro
            240                 245                 250
```

-continued

| | | |
|---|---|---|
| gtt ggc cgc aac gtc ctg gag ctc agc aat gtc gta cgc tct gcc aac<br>Val Gly Arg Asn Val Leu Glu Leu Ser Asn Val Val Arg Ser Ala Asn<br>255 260 265 | 1225 |
| tac acc tgt gtg gcc atc tcc tcg ctg ggc atg atc gag gcc aca gcc<br>Tyr Thr Cys Val Ala Ile Ser Ser Leu Gly Met Ile Glu Ala Thr Ala<br>270 275 280 285 | 1273 |
| cag gtc aca gtg aaa gct ctt cca aag cct ccg att gat ctt gtg gtg<br>Gln Val Thr Val Lys Ala Leu Pro Lys Pro Pro Ile Asp Leu Val Val<br>290 295 300 | 1321 |
| aca gag aca act gcc acc agt gtc acc ctc acc tgg gac tct ggg aac<br>Thr Glu Thr Thr Ala Thr Ser Val Thr Leu Thr Trp Asp Ser Gly Asn<br>305 310 315 | 1369 |
| tcg gag cct gta acc tac tat ggc atc cag tac cgc gca gcg ggc acg<br>Ser Glu Pro Val Thr Tyr Tyr Gly Ile Gln Tyr Arg Ala Ala Gly Thr<br>320 325 330 | 1417 |
| gag ggc ccc ttt cag gag gtg gat ggt gtg gcc acc acc cgc tac agc<br>Glu Gly Pro Phe Gln Glu Val Asp Gly Val Ala Thr Thr Arg Tyr Ser<br>335 340 345 | 1465 |
| att ggc ggc ctc agc cct ttc tcg gaa tat gcc ttc cgc gtg ctg gcg<br>Ile Gly Gly Leu Ser Pro Phe Ser Glu Tyr Ala Phe Arg Val Leu Ala<br>350 355 360 365 | 1513 |
| gtg aac agc atc ggg cga ggg ccg ccc agc gag gca gtg cgg gca cgc<br>Val Asn Ser Ile Gly Arg Gly Pro Pro Ser Glu Ala Val Arg Ala Arg<br>370 375 380 | 1561 |
| acg gga gaa cag gcg ccc tcc agc cca ccg cgc cgt gtg cag gca cgc<br>Thr Gly Glu Gln Ala Pro Ser Ser Pro Pro Arg Arg Val Gln Ala Arg<br>385 390 395 | 1609 |
| atg ctg agc gcc agc acc atg ctg gtg cag tgg gag cct ccc gag gag<br>Met Leu Ser Ala Ser Thr Met Leu Val Gln Trp Glu Pro Pro Glu Glu<br>400 405 410 | 1657 |
| ccc aac ggc ctg gtg cgg gga tac cgc gtc tac tat act ccg gac tcc<br>Pro Asn Gly Leu Val Arg Gly Tyr Arg Val Tyr Tyr Thr Pro Asp Ser<br>415 420 425 | 1705 |
| cgc cgc ccc ccg aac gcc tgg cac aag cac aac acc gac gcg ggg ctc<br>Arg Arg Pro Pro Asn Ala Trp His Lys His Asn Thr Asp Ala Gly Leu<br>430 435 440 445 | 1753 |
| ctc acg acc gtg ggc agc ctg ctg cct ggc atc acc tac agc ctg cgc<br>Leu Thr Thr Val Gly Ser Leu Leu Pro Gly Ile Thr Tyr Ser Leu Arg<br>450 455 460 | 1801 |
| gtg ctt gcc ttc acc gcc gtg ggc gat ggc cct ccc agc ccc acc atc<br>Val Leu Ala Phe Thr Ala Val Gly Asp Gly Pro Pro Ser Pro Thr Ile<br>465 470 475 | 1849 |
| cag gtc aag acg cag cag gga gtg cct gcc cag ccc gcg gac ttc cag<br>Gln Val Lys Thr Gln Gln Gly Val Pro Ala Gln Pro Ala Asp Phe Gln<br>480 485 490 | 1897 |
| gcc gag gtg gag tcg gac acc agg atc cag ctc tcg tgg ctg ctg ccc<br>Ala Glu Val Glu Ser Asp Thr Arg Ile Gln Leu Ser Trp Leu Leu Pro<br>495 500 505 | 1945 |
| cct cag gag cgg atc atc atg tat gaa ctg gtg tac tgg gcg gca gag<br>Pro Gln Glu Arg Ile Ile Met Tyr Glu Leu Val Tyr Trp Ala Ala Glu<br>510 515 520 525 | 1993 |
| gac gaa gac caa cag cac aag gtc acc ttc gac cca acc tcc tcc tac<br>Asp Glu Asp Gln Gln His Lys Val Thr Phe Asp Pro Thr Ser Ser Tyr<br>530 535 540 | 2041 |
| aca cta gag gac ctg aag cct gac aca ctc tac cgc ttc cag ctg gct<br>Thr Leu Glu Asp Leu Lys Pro Asp Thr Leu Tyr Arg Phe Gln Leu Ala<br>545 550 555 | 2089 |
| gca cgc tcg gat atg ggg gtg ggc gtc ttc acc ccc acc att gag gcc<br>Ala Arg Ser Asp Met Gly Val Gly Val Phe Thr Pro Thr Ile Glu Ala | 2137 |

```
                 560                565                570
cgc aca gcc cag tcc acc ccc tcc gcc cct ccc cag aag gtg atg tgt    2185
Arg Thr Ala Gln Ser Thr Pro Ser Ala Pro Pro Gln Lys Val Met Cys
575                 580                585 gtg agc atg ggc tcc acc acg gtc cgg gta agt tgg gtc ccg ccg cct    2233
Val Ser Met Gly Ser Thr Thr Val Arg Val Ser Trp Val Pro Pro Pro
590                 595                600                605 gcc gac agc cgc aac ggc gtt atc acc cag tac tcc gtg gcc cac gag    2281
Ala Asp Ser Arg Asn Gly Val Ile Thr Gln Tyr Ser Val Ala His Glu
                610                615                620 gcg gtg gac ggc gag gac cgc ggg cgg cat gtg gtg gat ggc atc agc    2329
Ala Val Asp Gly Glu Asp Arg Gly Arg His Val Val Asp Gly Ile Ser
            625                630                635 cgt gag cac tcc agc tgg gac ctg gtg ggc ctg gag aag tgg acg gag    2377
Arg Glu His Ser Ser Trp Asp Leu Val Gly Leu Glu Lys Trp Thr Glu
        640                645                650 tac cgg gtg tgg gtg cgg gca cac aca gac gtg ggc ccc ggc ccc gag    2425
Tyr Arg Val Trp Val Arg Ala His Thr Asp Val Gly Pro Gly Pro Glu
655                660                665 agc agc ccg gtg ctg gtg cgc acc gat gag gac gtg ccc agc ggg cct    2473
Ser Ser Pro Val Leu Val Arg Thr Asp Glu Asp Val Pro Ser Gly Pro
670                675                680                685 ccg cgg aag gtg gag gtg gag cca ctg aac tcc act gct gtg cat gtc    2521
Pro Arg Lys Val Glu Val Glu Pro Leu Asn Ser Thr Ala Val His Val
                690                695                700 tac tgg aag ctg cct gtc ccc agc aag cag cat ggc cag atc cgc ggc    2569
Tyr Trp Lys Leu Pro Val Pro Ser Lys Gln His Gly Gln Ile Arg Gly
            705                710                715 tac cag gtc acc tac gtg cgg ctg gag aat ggc gag ccc cgt gga ctc    2617
Tyr Gln Val Thr Tyr Val Arg Leu Glu Asn Gly Glu Pro Arg Gly Leu
        720                725                730 ccc atc atc caa gac gtc atg cta gcc gag gcc cag tgg cgg cca gag    2665
Pro Ile Ile Gln Asp Val Met Leu Ala Glu Ala Gln Trp Arg Pro Glu
735                740                745 gag tcc gag gac tat gaa acc act atc agc ggc ctg acc ccg gag acc    2713
Glu Ser Glu Asp Tyr Glu Thr Thr Ile Ser Gly Leu Thr Pro Glu Thr
750                755                760                765 acc tac tcc gtt act gtt gct gcc tat acc acc aag ggg gat ggt gcc    2761
Thr Tyr Ser Val Thr Val Ala Ala Tyr Thr Thr Lys Gly Asp Gly Ala
                770                775                780 cgc agc aag ccc aaa att gtc act aca aca ggt gca gtc cca ggc cgg    2809
Arg Ser Lys Pro Lys Ile Val Thr Thr Thr Gly Ala Val Pro Gly Arg
            785                790                795 ccc acc atg atg atc agc acc acg gcc atg aac act gcg ctg ctc cag    2857
Pro Thr Met Met Ile Ser Thr Thr Ala Met Asn Thr Ala Leu Leu Gln
        800                805                810 tgg cac cca ccc aag gaa ctg cct ggc gag ctg ctg ggc tac cgg ctg    2905
Trp His Pro Pro Lys Glu Leu Pro Gly Glu Leu Leu Gly Tyr Arg Leu
815                820                825 cag tac tgc cgg gcc gac gag gcg cgg ccc aac acc ata gat ttc ggc    2953
Gln Tyr Cys Arg Ala Asp Glu Ala Arg Pro Asn Thr Ile Asp Phe Gly
830                835                840                845 aag gat gac cag cac ttc aca gtc acc ggc ctg cac aag ggg acc acc    3001
Lys Asp Asp Gln His Phe Thr Val Thr Gly Leu His Lys Gly Thr Thr
                850                855                860 tac atc ttc cgg ctt gct gcc aag aac cgg gct ggc ttg ggt gag gag    3049
Tyr Ile Phe Arg Leu Ala Ala Lys Asn Arg Ala Gly Leu Gly Glu Glu
            865                870                875 ttc gag aag gag atc agg acc ccc gag gac ctg ccc agc ggc ttc ccc    3097
```

```
                Phe Glu Lys Glu Ile Arg Thr Pro Glu Asp Leu Pro Ser Gly Phe Pro
                            880                 885                 890 caa aac ctg cat gtg aca gga ctg acc acg tct acc aca gaa ctg gcc          3145
Gln Asn Leu His Val Thr Gly Leu Thr Thr Ser Thr Thr Glu Leu Ala
895                 900                 905 tgg gac ccg cca gtg ctg gcg gag agg aac ggg cgc atc atc agc tac          3193
Trp Asp Pro Pro Val Leu Ala Glu Arg Asn Gly Arg Ile Ile Ser Tyr
910                 915                 920                 925 acc gtg gtg ttc cga gac atc aac agc caa cag gag ctg cag aac atc          3241
Thr Val Val Phe Arg Asp Ile Asn Ser Gln Gln Glu Leu Gln Asn Ile
                930                 935                 940 acg aca gac acc cgc ttt acc ctt act ggc ctc aag cca gac acc act          3289
Thr Thr Asp Thr Arg Phe Thr Leu Thr Gly Leu Lys Pro Asp Thr Thr
            945                 950                 955 tac gac atc aag gtc cgc gca tgg acc agc aaa ggc tct ggc cca ctc          3337
Tyr Asp Ile Lys Val Arg Ala Trp Thr Ser Lys Gly Ser Gly Pro Leu
        960                 965                 970 agc ccc agc atc cag tcc cgg acc atg ccg gtg gag caa gtg ttt gcc          3385
Ser Pro Ser Ile Gln Ser Arg Thr Met Pro Val Glu Gln Val Phe Ala
    975                 980                 985 aag aac ttc cgg gtg gcg gct gca atg aag acg tct gtg ctg ctc agc          3433
Lys Asn Phe Arg Val Ala Ala Ala Met Lys Thr Ser Val Leu Leu Ser
990                 995                 1000                1005 tgg gag gtt ccc gac tcc tat aag tca gct gtg ccc ttt aag att ctg          3481
Trp Glu Val Pro Asp Ser Tyr Lys Ser Ala Val Pro Phe Lys Ile Leu
                1010                1015                1020 tac aat ggg cag agt gtg gag gtg gac ggg cac tcg atg cgg aag ctg          3529
Tyr Asn Gly Gln Ser Val Glu Val Asp Gly His Ser Met Arg Lys Leu
            1025                1030                1035 atc gca gac ctg cag ccc aac aca gag tac tcg ttt gtg ctg atg aac          3577
Ile Ala Asp Leu Gln Pro Asn Thr Glu Tyr Ser Phe Val Leu Met Asn
        1040                1045                1050 cgt ggc agc agc gca ggg ggc ctg cag cac ctg gtg tcc atc cgc aca          3625
Arg Gly Ser Ser Ala Gly Gly Leu Gln His Leu Val Ser Ile Arg Thr
    1055                1060                1065 gcc ccc gac ctc ctg cct cac aag ccg ctg cct gcc tct gcc tac ata          3673
Ala Pro Asp Leu Leu Pro His Lys Pro Leu Pro Ala Ser Ala Tyr Ile
1070                1075                1080                1085 gag gac ggc cgc ttc gat ctc tcc atg ccc cat gtg caa gac ccc tcg          3721
Glu Asp Gly Arg Phe Asp Leu Ser Met Pro His Val Gln Asp Pro Ser
                1090                1095                1100 ctt gtc agg tgg ttc tac att gtt gtg gta ccc att gac cgt gtg ggc          3769
Leu Val Arg Trp Phe Tyr Ile Val Val Val Pro Ile Asp Arg Val Gly
            1105                1110                1115 ggg agc atg ctg acg cca agg tgg agc aca ccc gag gaa ctg gag ctg          3817
Gly Ser Met Leu Thr Pro Arg Trp Ser Thr Pro Glu Glu Leu Glu Leu
        1120                1125                1130 gac gag ctt cta gaa gcc atc gag caa ggc gga gag gag cag cgg cgg          3865
Asp Glu Leu Leu Glu Ala Ile Glu Gln Gly Gly Glu Glu Gln Arg Arg
    1135                1140                1145 cgg cgg cgg cag gca gaa cgt ctg aag cca tat gtg gct gct caa ctg          3913
Arg Arg Arg Gln Ala Glu Arg Leu Lys Pro Tyr Val Ala Ala Gln Leu
1150                1155                1160                1165 gat gtg ctc ccg gag acc ttt acc ttg ggg gac aag aag aac tac cgg          3961
Asp Val Leu Pro Glu Thr Phe Thr Leu Gly Asp Lys Lys Asn Tyr Arg
                1170                1175                1180 ggc ttc tac aac cgg ccc ctg tct ccg gac ttg agc tac cag tgc ttt          4009
Gly Phe Tyr Asn Arg Pro Leu Ser Pro Asp Leu Ser Tyr Gln Cys Phe
            1185                1190                1195
```

```
gtg ctt gcc tcc ttg aag gaa ccc atg gac cag aag cgc tat gcc tcc    4057
Val Leu Ala Ser Leu Lys Glu Pro Met Asp Gln Lys Arg Tyr Ala Ser
    1200            1205            1210 agc ccc tac tcg gat gag atc gtg gtc cag gtg aca cca gcc cag cag    4105
Ser Pro Tyr Ser Asp Glu Ile Val Val Gln Val Thr Pro Ala Gln Gln
1215            1220            1225 cag gag gag ccg gag atg ctg tgg gtg acg ggt ccc gtg ctg gca gtc    4153
Gln Glu Glu Pro Glu Met Leu Trp Val Thr Gly Pro Val Leu Ala Val
1230            1235            1240            1245 atc ctc atc atc ctc att gtc atc gcc atc ctc ttg ttc aaa agg aaa    4201
Ile Leu Ile Ile Leu Ile Val Ile Ala Ile Leu Leu Phe Lys Arg Lys
                1250            1255            1260 agg acc cac tct ccg tcc tct aag gat gag cag tcg atc gga ctg aag    4249
Arg Thr His Ser Pro Ser Ser Lys Asp Glu Gln Ser Ile Gly Leu Lys
            1265            1270            1275 gac tcc ttg ctg gcc cac tcc tct gac cct gtg gag atg cgg agg ctc    4297
Asp Ser Leu Leu Ala His Ser Ser Asp Pro Val Glu Met Arg Arg Leu
        1280            1285            1290 aac tac cag acc cca ggt atg cga gac cac cca ccc atc ccc atc acc    4345
Asn Tyr Gln Thr Pro Gly Met Arg Asp His Pro Pro Ile Pro Ile Thr
    1295            1300            1305 gac ctg gcg gac aac atc gag cgc ctc aaa gcc aac gat ggc ctc aag    4393
Asp Leu Ala Asp Asn Ile Glu Arg Leu Lys Ala Asn Asp Gly Leu Lys
1310            1315            1320            1325 ttc tcc cag gag tat gag tcc atc gac cct gga cag cag ttc acg tgg    4441
Phe Ser Gln Glu Tyr Glu Ser Ile Asp Pro Gly Gln Gln Phe Thr Trp
                1330            1335            1340 gag aat tca aac ctg gag gtg aac aag ccc aag aac cgc tat gcg aat    4489
Glu Asn Ser Asn Leu Glu Val Asn Lys Pro Lys Asn Arg Tyr Ala Asn
            1345            1350            1355 gtc atc gcc tac gac cac tct cga gtc atc ctt acc tct atc gat ggc    4537
Val Ile Ala Tyr Asp His Ser Arg Val Ile Leu Thr Ser Ile Asp Gly
        1360            1365            1370 gtc ccc ggg agt gac tac atc aat gcc aac tac atc gat ggc tac cgc    4585
Val Pro Gly Ser Asp Tyr Ile Asn Ala Asn Tyr Ile Asp Gly Tyr Arg
    1375            1380            1385 aag cag aat gcc tac atc gcc acg cag ggc ccc ctg ccc gag acc atg    4633
Lys Gln Asn Ala Tyr Ile Ala Thr Gln Gly Pro Leu Pro Glu Thr Met
1390            1395            1400            1405 ggc gat ttc tgg aga atg gtg tgg gaa cag cgc acg gcc act gtg gtc    4681
Gly Asp Phe Trp Arg Met Val Trp Glu Gln Arg Thr Ala Thr Val Val
                1410            1415            1420 atg atg aca cgg ctg gag gag aag tcc cgg gta aaa tgt gat cag tac    4729
Met Met Thr Arg Leu Glu Glu Lys Ser Arg Val Lys Cys Asp Gln Tyr
            1425            1430            1435 tgg cca gcc cgt ggc acc gag acc tgt ggc ctt att cag gtg acc ctg    4777
Trp Pro Ala Arg Gly Thr Glu Thr Cys Gly Leu Ile Gln Val Thr Leu
        1440            1445            1450 ttg gac aca gtg gag ctg gcc aca tac act gtg cgc acc ttc gca ctc    4825
Leu Asp Thr Val Glu Leu Ala Thr Tyr Thr Val Arg Thr Phe Ala Leu
    1455            1460            1465 cac aag agt ggc tcc agt gag aag cgt gag ctg cgt cag ttt cag ttc    4873
His Lys Ser Gly Ser Ser Glu Lys Arg Glu Leu Arg Gln Phe Gln Phe
1470            1475            1480            1485 atg gcc tgg cca gac cat gga gtt cct gag tac cca act ccc atc ctg    4921
Met Ala Trp Pro Asp His Gly Val Pro Glu Tyr Pro Thr Pro Ile Leu
                1490            1495            1500 gcc ttc cta cga cgg gtc aag gcc tgc aac ccc cta gac gca ggg ccc    4969
Ala Phe Leu Arg Arg Val Lys Ala Cys Asn Pro Leu Asp Ala Gly Pro
            1505            1510            1515
```

-continued

| | |
|---|---|
| atg gtg gtg cac tgc agc gcg ggc gtg ggc cgc acc ggc tgc ttc atc<br>Met Val Val His Cys Ser Ala Gly Val Gly Arg Thr Gly Cys Phe Ile<br>　　　1520　　　　　　　　　1525　　　　　　　　　1530 | 5017 |
| gtg att gat gcc atg ttg gag cgg atg aag cac gag aag acg gtg gac<br>Val Ile Asp Ala Met Leu Glu Arg Met Lys His Glu Lys Thr Val Asp<br>1535　　　　　　　　　1540　　　　　　　　　1545 | 5065 |
| atc tat ggc cac gtg acc tgc atg cga tca cag agg aac tac atg gtg<br>Ile Tyr Gly His Val Thr Cys Met Arg Ser Gln Arg Asn Tyr Met Val<br>1550　　　　　　　　　1555　　　　　　　　　1560　　　　　　　　　1565 | 5113 |
| cag acg gag gac cag tac gtg ttc atc cat gag gcg ctg ctg gag gct<br>Gln Thr Glu Asp Gln Tyr Val Phe Ile His Glu Ala Leu Leu Glu Ala<br>　　　1570　　　　　　　　　1575　　　　　　　　　1580 | 5161 |
| gcc acg tgc ggc cac aca gag gtg cct gcc cgc aac ctg tat gcc cac<br>Ala Thr Cys Gly His Thr Glu Val Pro Ala Arg Asn Leu Tyr Ala His<br>1585　　　　　　　　　1590　　　　　　　　　1595 | 5209 |
| atc cag aag ctg ggc caa gtg cct cca ggg gag agt gtg acc gcc atg<br>Ile Gln Lys Leu Gly Gln Val Pro Pro Gly Glu Ser Val Thr Ala Met<br>1600　　　　　　　　　1605　　　　　　　　　1610 | 5257 |
| gag ctc gag ttc aag ttg ctg gcc agc tcc aag gcc cac acg tcc cgc<br>Glu Leu Glu Phe Lys Leu Leu Ala Ser Ser Lys Ala His Thr Ser Arg<br>　　　1615　　　　　　　　　1620　　　　　　　　　1625 | 5305 |
| ttc atc agc gcc aac ctg ccc tgc aac aag ttc aag aac cgg ctg gtg<br>Phe Ile Ser Ala Asn Leu Pro Cys Asn Lys Phe Lys Asn Arg Leu Val<br>1630　　　　　　　　　1635　　　　　　　　　1640　　　　　　　　　1645 | 5353 |
| aac atc atg ccc tac gaa ttg acc cgt gtg tgt ctg cag ccc atc cgt<br>Asn Ile Met Pro Tyr Glu Leu Thr Arg Val Cys Leu Gln Pro Ile Arg<br>　　　1650　　　　　　　　　1655　　　　　　　　　1660 | 5401 |
| ggt gtg gag ggc tct gac tac atc aat gcc agc ttc ctg gat ggt tat<br>Gly Val Glu Gly Ser Asp Tyr Ile Asn Ala Ser Phe Leu Asp Gly Tyr<br>1665　　　　　　　　　1670　　　　　　　　　1675 | 5449 |
| aga cag cag aag gcc tac ata gct aca cag ggg cct ctg gca gag agc<br>Arg Gln Gln Lys Ala Tyr Ile Ala Thr Gln Gly Pro Leu Ala Glu Ser<br>　　　1680　　　　　　　　　1685　　　　　　　　　1690 | 5497 |
| acc gag gac ttc tgg cgc atg cta tgg gag cac aat tcc acc atc atc<br>Thr Glu Asp Phe Trp Arg Met Leu Trp Glu His Asn Ser Thr Ile Ile<br>1695　　　　　　　　　1700　　　　　　　　　1705 | 5545 |
| gtc atg ctg acc aag ctt cgg gag atg ggc agg gag aaa tgc cac cag<br>Val Met Leu Thr Lys Leu Arg Glu Met Gly Arg Glu Lys Cys His Gln<br>1710　　　　　　　　　1715　　　　　　　　　1720　　　　　　　　　1725 | 5593 |
| tac tgg cca gca gag cgc tct gct cgc tac cag tac ttt gtt gtt gac<br>Tyr Trp Pro Ala Glu Arg Ser Ala Arg Tyr Gln Tyr Phe Val Val Asp<br>　　　1730　　　　　　　　　1735　　　　　　　　　1740 | 5641 |
| ccg atg gct gag tac aac atg ccc cag tat atc ctg cgt gag ttc aag<br>Pro Met Ala Glu Tyr Asn Met Pro Gln Tyr Ile Leu Arg Glu Phe Lys<br>1745　　　　　　　　　1750　　　　　　　　　1755 | 5689 |
| gtc acg gat gcc cgg gat ggg cag tca agg aca atc cgg cag ttc cag<br>Val Thr Asp Ala Arg Asp Gly Gln Ser Arg Thr Ile Arg Gln Phe Gln<br>　　　1760　　　　　　　　　1765　　　　　　　　　1770 | 5737 |
| ttc aca gac tgg cca gag cag ggc gtg ccc aag aca ggc gag gga ttc<br>Phe Thr Asp Trp Pro Glu Gln Gly Val Pro Lys Thr Gly Glu Gly Phe<br>1775　　　　　　　　　1780　　　　　　　　　1785 | 5785 |
| att gac ttc atc ggg cag gtg cat aag acc aag gag cag ttt gga cag<br>Ile Asp Phe Ile Gly Gln Val His Lys Thr Lys Glu Gln Phe Gly Gln<br>1790　　　　　　　　　1795　　　　　　　　　1800　　　　　　　　　1805 | 5833 |
| gat ggg cct atc acg gtg cac tgc agt gct ggc gtg ggc cgc acc ggg<br>Asp Gly Pro Ile Thr Val His Cys Ser Ala Gly Val Gly Arg Thr Gly<br>　　　1810　　　　　　　　　1815　　　　　　　　　1820 | 5881 |
| gtg ttc atc act ctg agc atc gtc ctg gag cgc atg cgc tat gag ggc<br>Val Phe Ile Thr Leu Ser Ile Val Leu Glu Arg Met Arg Tyr Glu Gly | 5929 |

-continued

| | |
|---|---|
| gtg gtc gac atg ttt cag acc gtg aag acc ctg cgt aca cag cgt cct<br>Val Val Asp Met Phe Gln Thr Val Lys Thr Leu Arg Thr Gln Arg Pro<br>  1840                         1845                      1850 | 5977 |
| gcc atg gtg cag aca gag gac cag tat cag ctg tgc tac cgt gcg gcc<br>Ala Met Val Gln Thr Glu Asp Gln Tyr Gln Leu Cys Tyr Arg Ala Ala<br>  1855                         1860                      1865 | 6025 |
| ctg gag tac ctc ggc agc ttt gac cac tat gca acg taactaccgc<br>Leu Glu Tyr Leu Gly Ser Phe Asp His Tyr Ala Thr<br>1870                      1875                      1880 | 6071 |
| tcccctctcc tccgccaccc ccgccgtggg gctccggagg ggacccagct cctctgagcc | 6131 |
| ataccgacca tcgtccagcc ctcctacgca gatgctgtca ctggcagagc acagcccacg | 6191 |
| gggatcacag cgtttcagga acgttgccac accaatcaga gagcctagaa catccctggg | 6251 |
| caagtggatg gcccagcagg caggcactgt ggcccttctg tccaccagac ccacctggag | 6311 |
| cccgcttcaa gctctctgtt gcgctcccgc atttctcatg cttcttctca tgggtgggg | 6371 |
| ttggggcaaa gcctcctttt taatacatta agtggggtag actgagggat tttagcctct | 6431 |
| tccctctgat ttttcctttc gcgaatccgt atctgcagaa tgggccactg tagggttgg | 6491 |
| ggtttatttt gttttgtttt tttttttttt ttgtatgact tctgctgaag gacagaacat | 6551 |
| tgccttcctc gtgcagagct ggggctgcca gcctgagcgg aggctcggcc gtgggccggg | 6611 |
| aggcagtgct gatccggctg ctcctccagc ccttcagacg agatcctgtt tcagctaaat | 6671 |
| gcagggaaac tcaatgtttt tttaagtttt gttttccctt taaagccttt ttttaggcca | 6731 |
| cattgacagt ggtgggcggg gagaagatag ggaacactca tccctggtcg tctatcccag | 6791 |
| tgtgtgttta acattcacag cccagaacca cagatgtgtc tgggagagcc tgcaaggca | 6851 |
| ttcctcatca ccatcgtgtt tgcaaaggtt aaaacaaaaa caaaaaacca caaaataaa | 6911 |
| aaacaaaaaa aacaaaaaac ccaaaaaaaa aaaaaaaag agtcagccct tggcttctgc | 6971 |
| ttcaaaccct caagagggga agcaactccg tgtgcctggg gttcccgagg gagctgctgg | 7031 |
| ctgacctggg cccacagagc ctggctttgg tccccagcat tgcagtatgg tgtggtgttt | 7091 |
| gtaggctgtg gggtctggct gtgtggccaa ggtgaatagc acaggttagg gtgtgtgcca | 7151 |
| cacccccatgc acctcaggggc caagcggggg cgtggctggc ctttcaggtc caggccagtg | 7211 |
| ggcctggtag cacatgtctg tcctcagagc aggggccaga tgattttcct ccctggtttg | 7271 |
| cagctgtttt caaagccccc gataatcgct cttttccact ccaagatgcc ctcataaacc | 7331 |
| aatgtggcaa gactactgga cttctatcaa tggtactcta atcagtcctt attatcccag | 7391 |
| cttgctgagg ggcagggaga gcgcctcttc ctctgggcag cgctatctag ataggtaagt | 7451 |
| gggggcgggg aagggtgcat agctgtttta gctgagggac gtggtgccga cgtccccaaa | 7511 |
| cctagctagg ctaagtcaag atcaacattc cagggttggt aatgttggat gatgaaacat | 7571 |
| tcatttttac cttgtggatg ctagtgctgt agagttcact gttgtacaca gtctgttttc | 7631 |
| tatttgttaa gaaaaactac agcatcattg cataattctt gatggtaata aatttgaata | 7691 |
| atcagatttc t | 7702 |

<210> SEQ ID NO 4
<211> LENGTH: 12
<212> TYPE: PRT
<213> ORGANISM: Unknown
<220> FEATURE:
<223> OTHER INFORMATION: Description of Unknown Organism: Identical
     Sequence in Phosphatase Domain 1 of LAR and CD45

-continued

```
<400> SEQUENCE: 4

Val Val His Cys Ser Ala Gly Val Gly Arg Thr Gly
 1               5                  10

<210> SEQ ID NO 5
<211> LENGTH: 6
<212> TYPE: PRT
<213> ORGANISM: Artificial sequence
<220> FEATURE:
<223> OTHER INFORMATION: Description of Unknown Organism: Consensus
      Amino Acid Sequence in Cytoplasmic Domain of Known PTPs.
<220> FEATURE:
<221> NAME/KEY: SITE
<222> LOCATION: (3)
<223> OTHER INFORMATION: Xaa= Arg, Glu or Leu
<220> FEATURE:
<221> NAME/KEY: SITE
<222> LOCATION: (5)
<223> OTHER INFORMATION: Xaa= Val, Ile or Cys

<400> SEQUENCE: 5

Phe Trp Xaa Met Xaa Trp
 1               5

<210> SEQ ID NO 6
<211> LENGTH: 7
<212> TYPE: PRT
<213> ORGANISM: Artificial sequence
<220> FEATURE:
<223> OTHER INFORMATION: Description of Unknown Organism: Consensus
      Amino Acid Sequence in Cytoplasmic Domain of Known PTPs.
<220> FEATURE:
<221> NAME/KEY: SITE
<222> LOCATION: (3)
<223> OTHER INFORMATION: Xaa= Ala or Asp
<220> FEATURE:
<221> NAME/KEY: SITE
<222> LOCATION: (4)
<223> OTHER INFORMATION: Xaa= Gln, Glu or Lys

<400> SEQUENCE: 6

Lys Cys Xaa Xaa Tyr Trp Pro
 1               5

<210> SEQ ID NO 7
<211> LENGTH: 6
<212> TYPE: PRT
<213> ORGANISM: Artificial sequence
<220> FEATURE:
<223> OTHER INFORMATION: Description of Unknown Organism: Consensus
      Amino Acid Sequence in Cytoplasmic Domain of Known PTPs.
<220> FEATURE:
<221> NAME/KEY: SITE
<222> LOCATION: (4)
<223> OTHER INFORMATION: Xaa= His or Phe

<400> SEQUENCE: 7

Trp Pro Asp Xaa Gly Val
 1               5

<210> SEQ ID NO 8
<211> LENGTH: 14
<212> TYPE: PRT
<213> ORGANISM: Artificial sequence
<220> FEATURE:
<223> OTHER INFORMATION: Description of Unknown Organism: Consensus
      Amino Acid Sequence in Cytoplasmic Domain of Known PTPs.
<220> FEATURE:
<221> NAME/KEY: SITE
<222> LOCATION: (2)
<223> OTHER INFORMATION: Xaa= Unkown
```

```
<220> FEATURE:
<221> NAME/KEY: SITE
<222> LOCATION: (3)
<223> OTHER INFORMATION: Xaa= Ile or Val
<220> FEATURE:
<221> NAME/KEY: SITE
<222> LOCATION: (4)
<223> OTHER INFORMATION: Xaa= Ile or Val
<220> FEATURE:
<221> NAME/KEY: SITE
<222> LOCATION: (7)
<223> OTHER INFORMATION: Xaa= Unkown
<220> FEATURE:
<221> NAME/KEY: SITE
<222> LOCATION: (10)
<223> OTHER INFORMATION: Xaa= Unknown
<220> FEATURE:
<221> NAME/KEY: SITE
<222> LOCATION: (13)
<223> OTHER INFORMATION: Xaa= Thr or Ser

<400> SEQUENCE: 8

Pro Xaa Xaa Xaa His Cys Xaa Ala Gly Xaa Gly Arg Xaa Gly
 1               5                  10

<210> SEQ ID NO 9
<211> LENGTH: 538
<212> TYPE: PRT
<213> ORGANISM: Homo sapiens

<400> SEQUENCE: 9

Ser Asn Leu Glu Val Asn Lys Pro Lys Asn Arg Tyr Ala Asn Val Ile
 1               5                  10                  15

Ala Tyr Asp His Ser Arg Val Ile Leu Thr Ser Ile Asp Gly Val Pro
                20                  25                  30

Gly Ser Asp Tyr Ile Asn Ala Asn Tyr Ile Asp Gly Tyr Arg Lys Gln
            35                  40                  45

Asn Ala Tyr Ile Ala Thr Gln Gly Pro Leu Pro Glu Thr Met Gly Asp
    50                  55                  60

Phe Trp Arg Met Val Trp Glu Gln Arg Thr Ala Thr Val Val Met Met
65                  70                  75                  80

Thr Arg Leu Glu Glu Lys Ser Arg Val Lys Cys Asp Gln Tyr Trp Pro
                85                  90                  95

Ala Arg Gly Thr Glu Thr Cys Gly Leu Ile Gln Val Thr Leu Leu Asp
            100                 105                 110

Thr Val Glu Leu Ala Thr Tyr Thr Val Arg Thr Phe Ala Leu His Lys
    115                 120                 125

Ser Gly Ser Ser Glu Lys Arg Glu Leu Arg Gln Phe Gln Phe Met Ala
130                 135                 140

Trp Pro Asp His Gly Val Pro Glu Tyr Pro Thr Pro Ile Leu Ala Phe
145                 150                 155                 160

Leu Arg Arg Val Lys Ala Cys Asn Pro Leu Asp Ala Gly Pro Met Val
                165                 170                 175

Val His Cys Ser Ala Gly Val Gly Arg Thr Gly Cys Phe Ile Val Ile
            180                 185                 190

Asp Ala Met Leu Glu Arg Met Lys His Glu Lys Thr Val Asp Ile Tyr
    195                 200                 205

Gly His Val Thr Cys Met Arg Ser Gln Arg Asn Tyr Met Val Gln Thr
210                 215                 220

Glu Asp Gln Tyr Val Phe Ile His Glu Ala Leu Leu Glu Ala Ala Thr
225                 230                 235                 240
```

-continued

Cys Gly His Thr Glu Val Pro Ala Arg Asn Leu Tyr Ala His Ile Gln
                245                 250                 255

Lys Leu Gly Gln Val Pro Pro Gly Glu Ser Val Thr Ala Met Glu Leu
            260                 265                 270

Glu Phe Lys Leu Leu Ala Ser Ser Lys Ala His Thr Ser Arg Phe Ile
        275                 280                 285

Ser Ala Asn Leu Pro Cys Asn Lys Phe Lys Asn Arg Leu Val Asn Ile
    290                 295                 300

Met Pro Tyr Glu Leu Thr Arg Val Cys Leu Gln Pro Ile Arg Gly Val
305                 310                 315                 320

Glu Gly Ser Asp Tyr Ile Asn Ala Ser Phe Leu Asp Gly Tyr Arg Gln
                325                 330                 335

Gln Lys Ala Tyr Ile Ala Thr Gln Gly Pro Leu Ala Glu Ser Thr Glu
            340                 345                 350

Asp Phe Trp Arg Met Leu Trp Glu His Asn Ser Thr Ile Ile Val Met
        355                 360                 365

Leu Thr Lys Leu Arg Glu Met Gly Arg Glu Lys Cys His Gln Tyr Trp
    370                 375                 380

Pro Ala Glu Arg Ser Ala Arg Tyr Gln Tyr Phe Val Val Asp Pro Met
385                 390                 395                 400

Ala Glu Tyr Asn Met Pro Gln Tyr Ile Leu Arg Glu Phe Lys Val Thr
                405                 410                 415

Asp Ala Arg Asp Gly Gln Ser Arg Thr Ile Arg Gln Phe Gln Phe Thr
            420                 425                 430

Asp Trp Pro Glu Gln Gly Val Pro Lys Thr Gly Glu Gly Phe Ile Asp
        435                 440                 445

Phe Ile Gly Gln Val His Lys Thr Lys Glu Gln Phe Gly Gln Asp Gly
    450                 455                 460

Pro Ile Thr Val His Cys Ser Ala Gly Val Gly Arg Thr Gly Val Phe
465                 470                 475                 480

Ile Thr Leu Ser Ile Val Leu Glu Arg Met Arg Tyr Glu Gly Val Val
                485                 490                 495

Asp Met Phe Gln Thr Val Lys Thr Leu Arg Thr Gln Arg Pro Ala Met
            500                 505                 510

Val Gln Thr Glu Asp Gln Tyr Gln Leu Cys Tyr Arg Ala Ala Leu Glu
        515                 520                 525

Tyr Leu Gly Ser Phe Asp His Tyr Ala Thr
    530                 535

<210> SEQ ID NO 10
<211> LENGTH: 635
<212> TYPE: PRT
<213> ORGANISM: Homo sapiens

<400> SEQUENCE: 10

Ala Arg Lys Pro Phe Asn Gln Asn Lys Asn Arg Tyr Val Asp Ile Leu
1               5                   10                  15

Pro Tyr Asp Tyr Asn Arg Val Glu Leu Ser Glu Ile Asn Gly Asp Ala
                20                  25                  30

Gly Ser Asn Tyr Ile Asn Ala Ser Tyr Ile Asp Gly Phe Lys Glu Pro
            35                  40                  45

Arg Lys Tyr Ile Ala Ala Gln Gly Pro Arg Asp Glu Thr Val Asp Asp
        50                  55                  60

Phe Trp Arg Met Ile Trp Glu Gln Lys Ala Thr Val Ile Val Met Val
65                  70                  75                  80

-continued

```
Thr Arg Cys Glu Glu Gly Asn Arg Asn Lys Cys Ala Glu Tyr Trp Pro
                85                  90                  95

Ser Met Glu Glu Gly Thr Arg Ala Phe Gly Asp Val Val Lys Ile
            100                 105                 110

Asn Gln His Lys Arg Cys Pro Asp Tyr Ile Ile Gln Lys Leu Asn Ile
            115                 120                 125

Val Asn Lys Lys Glu Lys Ala Thr Gly Arg Glu Val Thr His Ile Gln
    130                 135                 140

Phe Thr Ser Trp Pro Asp His Gly Val Pro Glu Asp Pro His Leu Leu
145                 150                 155                 160

Leu Lys Leu Arg Arg Arg Val Asn Ala Phe Ser Asn Phe Phe Ser Gly
                165                 170                 175

Pro Ile Val His Cys Ser Ala Gly Val Gly Arg Thr Gly Thr Tyr
            180                 185                 190

Ile Gly Ile Asp Ala Met Leu Glu Gly Leu Glu Ala Glu Asn Lys Val
        195                 200                 205

Asp Val Tyr Gly Tyr Val Val Lys Leu Arg Arg Gln Arg Cys Leu Met
    210                 215                 220

Val Gln Val Glu Ala Gln Tyr Ile Leu Ile His Gln Ala Leu Val Glu
225                 230                 235                 240

Tyr Asn Gln Phe Gly Glu Thr Glu Val Asn Leu Ser Glu Leu His Pro
                245                 250                 255

Tyr Leu His Asn Met Lys Lys Arg Asp Pro Pro Ser Glu Pro Ser Pro
            260                 265                 270

Leu Glu Ala Glu Phe Gln Arg Leu Pro Ser Tyr Arg Ser Trp Arg Thr
        275                 280                 285

Gln His Ile Gly Asn Gln Glu Glu Asn Lys Ser Lys Asn Arg Asn Ser
    290                 295                 300

Asn Val Ile Pro Tyr Asp Tyr Asn Arg Val Pro Leu Lys His Glu Leu
305                 310                 315                 320

Glu Met Ser Lys Glu Ser Glu His Asp Ser Asp Glu Ser Ser Asp Asp
                325                 330                 335

Asp Ser Asp Ser Glu Glu Pro Ser Lys Tyr Ile Asn Ala Ser Phe Ile
            340                 345                 350

Met Ser Tyr Trp Lys Pro Glu Val Met Ile Ala Ala Gln Gly Pro Leu
        355                 360                 365

Lys Glu Thr Ile Gly Asp Phe Trp Gln Met Ile Phe Gln Arg Lys Val
    370                 375                 380

Lys Val Ile Val Met Leu Thr Glu Leu Lys His Gly Asp Gln Glu Ile
385                 390                 395                 400

Cys Ala Gln Tyr Trp Gly Glu Gly Lys Gln Thr Tyr Gly Asp Ile Glu
                405                 410                 415

Val Asp Leu Lys Asp Thr Asp Lys Ser Ser Thr Tyr Thr Leu Arg Val
            420                 425                 430

Phe Glu Leu Arg His Ser Lys Arg Lys Asp Ser Arg Thr Val Tyr Gln
        435                 440                 445

Tyr Gln Tyr Thr Asn Trp Ser Val Glu Gln Leu Pro Ala Glu Pro Lys
    450                 455                 460

Glu Leu Ile Ser Met Ile Gln Val Val Lys Gln Lys Leu Pro Gln Lys
465                 470                 475                 480

Asn Ser Ser Glu Gly Asn Lys His His Lys Ser Thr Pro Leu Leu Ile
                485                 490                 495
```

-continued

```
His Cys Arg Asp Gly Ser Gln Gln Thr Gly Ile Phe Cys Ala Leu Leu
            500                 505             510

Asn Leu Leu Glu Ser Ala Glu Thr Glu Glu Val Val Asp Ile Phe Gln
        515                 520                 525

Val Val Lys Ala Leu Arg Lys Ala Arg Pro Gly Met Val Ser Thr Phe
    530                 535                 540

Glu Gln Tyr Gln Phe Leu Tyr Asp Val Ile Ala Ser Thr Tyr Pro Ala
545                     550                 555                 560

Gln Asn Gly Gln Val Lys Lys Asn Asn His Gln Glu Asp Lys Ile Glu
                565                 570                 575

Phe Asp Asn Glu Val Asp Lys Val Lys Gln Asp Ala Asn Cys Val Asn
            580                 585                 590

Pro Leu Gly Ala Pro Glu Lys Leu Pro Glu Ala Lys Glu Gln Ala Glu
        595                 600                 605

Gly Ser Glu Pro Thr Ser Gly Thr Glu Gly Pro Glu His Ser Val Asn
        610                 615                 620

Gly Pro Ala Ser Pro Ala Leu Asn Gln Gly Ser
625                 630                 635
```